US008540996B2

(12) United States Patent
Qian et al.

(10) Patent No.: US 8,540,996 B2
(45) Date of Patent: Sep. 24, 2013

(54) MONOCLONAL ANTIBODIES SPECIFIC TO HEMAGGLUTININ AND NEURAMINIDASE FROM INFLUENZA VIRUS H5-SUBTYPE OR N1-SUBTYPE AND USES THEREOF

(75) Inventors: Hong Liang Qian, Singapore (SG); Fang He, Singapore (SG); Hwei-Sing Kwang, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 0 days.

(21) Appl. No.: 13/610,054

(22) Filed: Sep. 11, 2012

(65) Prior Publication Data

US 2013/0004497 A1    Jan. 3, 2013

Related U.S. Application Data

(62) Division of application No. 12/677,971, filed as application No. PCT/SG2008/000347 on Sep. 12, 2008, now Pat. No. 8,383,121.

(60) Provisional application No. 60/972,059, filed on Sep. 13, 2007.

(51) Int. Cl.
*A61K 39/42* (2006.01)
*C07K 16/10* (2006.01)
*C12Q 1/70* (2006.01)

(52) U.S. Cl.
USPC ............... 424/147.1; 424/133.1; 530/388.3; 530/387.3; 530/389.4; 435/5

(58) Field of Classification Search
None
See application file for complete search history.

(56) References Cited

FOREIGN PATENT DOCUMENTS

| WO | 2007/021002 A1 | 2/2007 |
| WO | 2007/031550 A2 | 3/2007 |
| WO | 2007/089753 A2 | 8/2007 |
| WO | 2008/028946 A2 | 3/2008 |
| WO | 2008/140415 A1 | 11/2008 |
| WO | 2008/156763 A2 | 12/2008 |
| WO | 2009/035412 A1 | 3/2009 |

OTHER PUBLICATIONS

Kaverin et al (Journal of Virology 81:12911-12917, 2007).*
He et al (Clinical and Vaccine Immunology 14:617-623, 2007).*
Hanson et al (Respiratory Research 7:126:1-10, 2006).*
Kaverin et al (Journal of General Virology 83:4297-2505, 2002.*
Genbank ABI36428, hemagglutinin [Influenza A virus (A/Indonesia/CDC669/2006(H5N1))], Apr. 25, 2008.*
Genbank ABW90134, hemagglutinin [Influenza A virus (A/Viet Nam/1203/2004(H5N1))], isolate="escape mutant m15(20)", Nov. 14, 2007.*
Smirnov, Y. et al., An Epitope Shared by the Hemagglutinins of H1, H2, H5, and H6 Subtypes of Influenza A Virus, ACTA Virologica, vol. 43, No. 4, Aug. 1, 1999, pp. 237-244, XP009095964, Academia Prague, CS.
Sheng, Wu Gong Cheng Xue Bao, Chinese Journal of Biotechnology, vol. 23, No. 2, Mar. 2007, pp. 292-296.
Luo, Hai-Feng et al., "Characterization of a Broad-Spectrum Neutralization Monoclonal Antibody Against Haemagglutinin of H5 Subtype Avian Influenza Virus," Bingdu Xuebao—Chinese Journal of Virology, Zhongguo Weishengwu Xuchui, Beijing, CN, vol. 23, No. 2, Mar. 1, 2007, pp. 85-90, XP001525197 (abstract only), 1 page.
Hanson, Brendon J. et al., "Passive Immunoprophylaxis and Therapy with Humanized Monoclonal Antibody Specific for Influenza A H5 Hemagglutinin in Mice," Respiratory Research, vol. 7, No. 126, Jan. 1, 2006, pp. 1-10, XP002547473.
Extended European Search Report, Reference: HB/P42052EP, Appln No. 08830693.1-1222 / 2201039, PCT/SG2008000347, dated Mar. 14, 2012, Applicant: Temasek Life Sciences Limited, 19 pages.
Cameron, P. Simmons et al., "Prophylactic and Therapeutic Efficacy of Human Monoclonal Antibodies Against H5N1 Influenza," PLoS Medicine, May 29, 2007, vol. 4, Issue 5, pp. 928-936.
Qigai He et al., "Detection of H5 Avian Infuenza Viruses by Antigen-Capture Enzyme-Linked Immunosorbent Assay Using H5-Specific Monoclonal Antibody," Clinical and Vaccine Immunology, May 2007, vol. 14, No. 5, pp. 617-623.
Z. Fang et ai., "Preparation and Identification of a Single-Chain Antibody Fragment Against High Pathogenic H5N1 Avian Influenza Virus," Sheng wu gong cheng xue bao = Chinese Journal of Biotechnology, Mar. 2007, vol. 23, No. 2, pp. 292-296.
Matthew R. Sandbulte et al., "Cross-Reactive Neuraminidase Antibodies Afford Partial Protection Against H5N1 in Mice and Are Present in Unexposed Humans," PLoS Medicine, Feb. 13, 2007, vol. 4, Issue 2, pp. 265-272.
Written Opinion and Search Report, Intellectual Property Office of Singapore (IPOS), dated Sep. 16, 2011, Singapore Application No. 201001658-2, "Monoclonal Antibodies Specific to Hemagglutinin and Neuraminidase from Influenza Virus H5-Subtype or N1-Subtype and Uses Thereof," 15 pages.
Chen, Jianfeng et al., "A Latex Agglutination Test for the Rapid Detection of Avian Influenza Virus Subtype H5N1 and its Clinical Application," Journal of Veterinary Diagnostic Investigation, 19(3): 155-160 (May 1, 2007).
Yan, Juying et al., "Pathogenic and molecular characterization of the H5N1 avian influenza virus isolated from the first human case in Zhejiang province, China," Diagnostic Microbiology and Infectious Disease, 58(4): 399-405 (Aug. 2007).
Nettles, V., et al., "Wildlife Surveillance Associated with an Outbreak of Lethal H5N2 Avian Influenza in Domestic Poultry," Avian Diseases, 29(3): 733-41 (Jul.-Sep. 1985).
Zhenhua, Yang et al., "Expression of Neuraminidase of H5N1 subtype avian influenza virus and production of polyclonal antibody," Wuhan Daxue Xuebao, Lixueban, 53(4): 481-484 (Aug. 2007).
Horthongkham, N, et al., "Specific antibody response of mice after immunization with COS-7 cell derived avian influenza virus (H5N1) recombinant proteins," Journal of Immune Based Therapies and Vaccines, 5: p. 10 (Oct. 3, 2007)

(Continued)

*Primary Examiner* — Mary E Mosher
(74) *Attorney, Agent, or Firm* — Rothwell, Figg, Ernst & Manbeck P.C.

(57) ABSTRACT

Monoclonal antibodies and related binding proteins that bind specifically to the envelope glycoprotein of H5 subtypes or neuraminidase glycoprotein of N1 subtypes of avian influenza virus (AIV) are provided. The monoclonal antibodies and related binding proteins are useful for the detection of H5 and N1 subtypes of AIV, including H5N1 subtypes and provide means for the diagnosis, surveillance and treatment of dangerous viral infections.

24 Claims, 7 Drawing Sheets

(56) References Cited

OTHER PUBLICATIONS

Itoh, Y, et al., "A vaccine prepared from a non-pathogenic H5N1 avian influenza virus strain confers protective immunity against highly pathogenic avian influenza virus infection in cynomolgus macaques," Vaccine, 26(4): 562-72 (Jan. 24, 2008).

Laddy, D. J., et al., "Heterosubtypic Protection Against Pathogenic Human and Avian Influenza Viruses via In Vivo Electroporation of Synthetic Consensus DNA Antigens," PLoS ONE, 3(6): e2517 (Jun. 2008).

International Search Report and Written Opinion for PCT/SG2008/000347, mailed Nov. 24, 2008.

Simmons, C.P. et al., "Prophylactic and Therapeutic Efficacy of Human Monoclonal Antibodies Against H5N1 Influenza," PLoS Medicine, vol. 4, Issue 5, e178, pp. 0928-0936, May 2007.

Bui, H.H. et al., "Ab and T Cell Epitopes of Influenza A Virus, Knowledge and Opportunities," Proceedings of the National Academy of Science, Jan. 2, 2007, vol. 104, No. 1, pp. 246-251.

Nucleotide, "Influenza A Virus (A/Indonesia/CDC669/2006(H5N1) Segment 4 Sequence," The National Center for Biotechnology Information, Accession No. CY014481, [online], Aug. 30, 2006, <http://www.ncbi.nlm.nih.gov/nuccore/113497155?sat=12&satkey=4189293>,[retrieved on Jan. 29, 2013], 2 pages.

Goji, N. A. et al., "Immune Responses of Healthy Subjects to a Single Dose of Intramuscular Inactivated Influenza A/Vietnam/1203/2004 (H5N1) Vaccine After Priming With an Antigenic Variant," Journal of Infectious Diseases, Sep. 1, 2008, vol. 198, pp. 635-641.

Japanese Office Action and English Translation, JP Application No. 2010-524824; Drafting Date: Jan. 29, 2013; Dispatch Date: Feb. 1, 2013, 10 pages.

* cited by examiner

Figure 1A
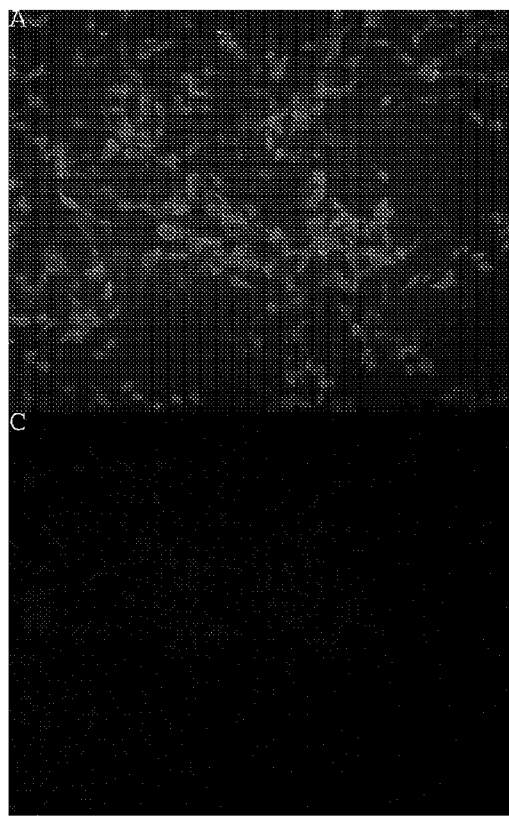
Figure 1C
Figure 1B
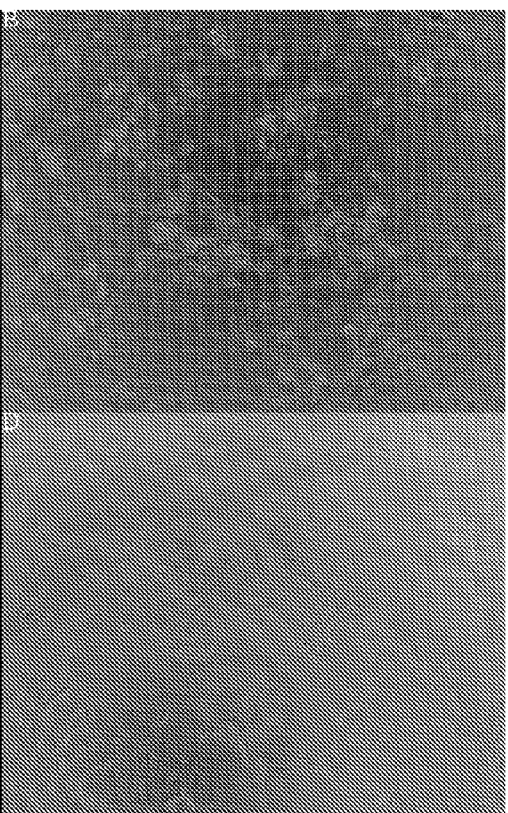
Figure 1D.

Figure 4A

|  | HA1 (A/goose/Guangdong/97 H5N1) | aa | Western Blot by 5A5 |
|---|---|---|---|
| 1 |  | 338 | + |
| 1 — A — 133 |  |  | -- |
| 67 — B — 271 |  |  | + |
| 201 — C — 338 |  |  | + |
| 67 — D — 248 |  |  | --- |
| 67 — E — 258 |  |  | -- |
| 67 — F — 262 |  |  | --- |
| 67 — G — 266 |  |  | -- |
| 67 — H — 276 |  |  | + |

Western by 5A5

| 259 S N G N F I A P E Y A Y K 271 | + |
| 259 S N G N F I A P E Y A Y A 271 | + |
| 259 S N G N F I A P E Y A A K 271 | + |
| 259 S N G N F I A P E Y P Y K 271 | — |
| 259 S N G N F I A P E A A Y K 271 | — |
| 259 S N G N F A A P E Y A Y K 271 | — |
| 259 S N G N A I A P E Y A Y K 271 | — |
| 259 S N G A F I A P E Y A Y K 271 | — |
| 259 S N A N F I A P E Y A Y K 271 | — |
| 259 S A G N F I A P E Y A Y K 271 | — |
| 259 A N G N F I A P E Y A Y K 271 | + |

Figure 4B

SEQUENCE LISTING

```
<160> NUMBER OF SEQ ID NOS: 13

<210> SEQ ID NO 1
<211> LENGTH: 31
<212> TYPE: DNA
<213> ORGANISM: Avian influenza virus

<400> SEQUENCE: 1
caccatgaat ccaaatcaga agataacaac c                              31

<210> SEQ ID NO 2
<211> LENGTH: 21
<212> TYPE: DNA
<213> ORGANISM: Avian influenza virus

<400> SEQUENCE: 2
cttgtcaatg gtgaatggca a                                         21

<210> SEQ ID NO 3
<211> LENGTH: 13
<212> TYPE: PRT
<213> ORGANISM: Avian influenza virus

<400> SEQUENCE: 3

Ser Asn Gly Asn Phe Ile Ala Pro Glu Tyr Ala Tyr Lys
1               5                   10

<210> SEQ ID NO 4
<211> LENGTH: 13
<212> TYPE: PRT
```

<213> ORGANISM: Avian influenza virus

<400> SEQUENCE: 4

Ser Asn Gly Asn Phe Ile Ala Pro Glu Tyr Ala Tyr Ala
1               5                   10

<210> SEQ ID NO 5
<211> LENGTH: 13
<212> TYPE: PRT
<213> ORGANISM: Avian influenza virus

<400> SEQUENCE: 5

Ser Asn Gly Asn Phe Ile Ala Pro Glu Tyr Ala Ala Lys
1               5                   10

<210> SEQ ID NO 6
<211> LENGTH: 13
<212> TYPE: PRT
<213> ORGANISM: Avian influenza virus

<400> SEQUENCE: 6

Ser Asn Gly Asn Phe Ile Ala Pro Glu Tyr Pro Tyr Lys
1               5                   10

<210> SEQ ID NO 7
<211> LENGTH: 13
<212> TYPE: PRT
<213> ORGANISM: Avian influenza virus

<400> SEQUENCE: 7

Ser Asn Gly Asn Phe Ile Ala Pro Glu Ala Ala Tyr Lys
1               5                   10

<210> SEQ ID NO 8
<211> LENGTH: 13
<212> TYPE: PRT
<213> ORGANISM: Avian influenza virus

<400> SEQUENCE: 8

Ser Asn Gly Asn Phe Ala Ala Pro Glu Tyr Ala Tyr Lys
1               5                   10

<210> SEQ ID NO 9
<211> LENGTH: 13
<212> TYPE: PRT
<213> ORGANISM: Avian influenza virus

<400> SEQUENCE: 9

Ser Asn Gly Asn Ala Ile Ala Pro Glu Tyr Ala Tyr Lys
1               5                   10

<210> SEQ ID NO 10
<211> LENGTH: 13
<212> TYPE: PRT
<213> ORGANISM: Avian influenza virus

<400> SEQUENCE: 10

Ser Asn Gly Ala Phe Ile Ala Pro Glu Tyr Ala Tyr Lys
1               5                   10

<210> SEQ ID NO 11
<211> LENGTH: 13
<212> TYPE: PRT
<213> ORGANISM: Avian influenza virus

<400> SEQUENCE: 11

```
Ser Asn Ala Asn Phe Ile Ala Pro Glu Tyr Ala Tyr Lys
1               5                   10

<210> SEQ ID NO 12
<211> LENGTH: 13
<212> TYPE: PRT
<213> ORGANISM: Avian influenza virus

<400> SEQUENCE: 12

Ser Ala Gly Asn Phe Ile Ala Pro Glu Tyr Ala Tyr Lys
1               5                   10

<210> SEQ ID NO 13
<211> LENGTH: 13
<212> TYPE: PRT
<213> ORGANISM: Avian influenza virus

<400> SEQUENCE: 13

Ala Asn Gly Asn Phe Ile Ala Pro Glu Tyr Ala Tyr Lys
1               5                   10
```

MONOCLONAL ANTIBODIES SPECIFIC TO HEMAGGLUTININ AND NEURAMINIDASE FROM INFLUENZA VIRUS H5-SUBTYPE OR N1-SUBTYPE AND USES THEREOF

CROSS-REFERENCE TO RELATED APPLICATIONS

The present application is a division of U.S. patent application Ser. No. 12/677,971 filed 12 Mar. 2010 which in turn is a filing under 35 USC 371 of PCT/SG2008/000347, filed 12 Sep. 2008, which in turn claims priority to U.S. Provisional Application Ser. No. 60/972,059, filed 13 Sep. 2007. Each application is incorporated herein in its entirety.

SEQUENCE SUBMISSION

The present application is being filed along with a Sequence Listing in electronic format. The Sequence Listing is entitled 2577220SequenceListing.txt, created on 17 Jul. 2013 and is 3 kb in size. The information in the electronic format of the Sequence Listing is incorporated herein by reference in its entirety.

FIELD OF THE INVENTION

This invention relates to antibodies and related binding proteins for the detection and treatment of avian influenza virus ("AIV"). More particularly, this invention relates to monoclonal antibodies and related binding proteins useful for the detection and treatment of the highly pathogenic H5 and N1 subtypes of AIV and to methods and products for the diagnosis, surveillance and treatment of AIV infections in animals and humans.

BACKGROUND OF THE INVENTION

H5N1 avian influenza virus may become the cause of the next flu pandemic. Annual outbreaks of influenza A infection are an ongoing public health threat and novel influenza strains can emerge periodically to which humans have little immunity, resulting in devastating pandemics. The "Spanish flu" pandemic of 1918, caused by the H1N1 influenza virus, killed more than 40 million people world-wide. The origin of H1N1 may have gone directly from birds to humans, or it may have involved incubation in an intermediate host, such as the pig or another, as yet unidentified, animal host (1). Both the 1957 pandemic and the 1968 pandemic, caused by the H2N2 and H3N2 influenza viruses, respectively, likely originated as reassortments in which one or both human-adapted viral surface proteins were replaced by proteins from avian influenza strains (2).

The H5N1 virus has the ability to infect an unprecedented range of hosts, including carnivores. The first confirmed instances of AIV H5N1 infecting humans took place in 1997. Highly pathogenic H5N1 infections occurred in both poultry and humans. This was the first time an avian influenza virus transmission directly from birds to humans had been found. Thereafter, according to the World Health Organization (WHO), the total number of human H5N1 cases, since the initial outbreaks in south-east Asia which occurred in 2003, has reached 281, with 169 deaths. Indonesia reported its first human case of avian flu caused by the H5N1 virus in June of 2005. To date, it is the only country to report cases in 2007, with 81 confirmed human cases, 63 of which were fatal, as of March, 2007.

Influenza viruses are classified according to their nucleoprotein and matrix protein antigenic specificity. These viruses are categorized mainly into A, B and C serotypes, with type A having eight RNA segments that encode ten viral proteins. All known type A influenza viruses originated in birds. This category of virus can infect other species, such as horses, pigs, owls and seals, and poses a threat to humans as well (23). Influenza A virus is further divided into subtypes according to the antigenic nature of the envelope glycoproteins, hemagglutinins ("HAs"), H1 through H16, and neuraminidases ("NAs"), N1 through N9 (24, 25, 26). It is believed that proteolytic cleavage of HA protein at the HA1-HA2 junction is related to the pathogenicity in avian strain and that the presence of hydrophobic amino acids around this cleavage site are characteristic of the H5 subtype. In addition, the HA protein is believed to mediate attachments to host cell sialoside receptors and subsequent entry by membrane fusion (27), and HA protein is thought to serve as a primary target for neutralizing antibodies (26).

Testing during an outbreak of an acute respiratory disease can determine if influenza is the cause. During influenza season, testing of selected patients presenting with respiratory illnesses compatible with influenza can help establish whether influenza is present in a specific patient population and help health-care providers determine how to use their clinical judgment for diagnosing and treating respiratory illness. A rapid influenza test helps in the determination of whether to use an antiviral medication. Some tests, such as a viral culture, reverse-transcriptase polymerase chain reaction (RT-PCR) and serological testing are the routine methods, but results may not be available in a timely manner to assist clinicians (3). At present, most of the rapid diagnostic tests currently in use are monoclonal antibody-based immunoassays (3, 4, 5). Immunofluorescence (fluorescent antibody staining) is the alternative to rapid influenza diagnostic tests which can be used in many hospital laboratories and generally can yield test results in 2-4 hours. Above all, specific monoclonal antibody generation is fundamental to most currently used rapid, sensitive and cost-effective diagnostic methods.

The identification of regionally distinct sublineages has indicated that the H5N1 virus is geographically broad with great genetic and antigenic diversity. Phylogenetic analysis showing that all viruses from Indonesia form a distinct sublineage of H5N1 genotype Z viruses suggests that this outbreak likely originated from a single introduction that spread throughout the country (14, 15). It would be very useful to have available monoclonal antibodies which specifically recognize Indonesia influenza isolates. It further would be useful to have available such mAbs which also cover Vietnam and Singapore influenza isolates.

OBJECTS OF THE INVENTION

An object of this invention is to provide monoclonal antibodies ("mAbs") and related binding proteins that bind specifically to H5 and N1 subtypes of AIV, particularly to H5 and N1 Indonesia AIV isolates. The specificity of monoclonal antibody responses provides a basis for effective diagnostic reagents. MAbs and binding proteins derived therefrom also can be useful as therapeutic agents.

SUMMARY OF THE INVENTION

In accordance with the present invention, monoclonal antibodies and related binding proteins that are specific for linear and conformational epitopes of the H5 subtype hemagglutinin glycoprotein or linear and conformational epitopes of the N1 subtype neuraminidase glycoprotein are provided. MAbs to linear H5 epitopes are able to detect H5N1 and other H5 subtype virus strains in denatured specimens, such as formalin-fixed tissue specimens, with good specificity and sensitivity, while those that target H5 or N1 conformational epitopes are useful for detecting H5N1 and other N1 subtype virus in tissues which have not been pre-treated, such as frozen tissue specimens and other biological tissues and fluids. MAbs to H5 epitopes and mAbs to N1 epitopes can be used in combination to specifically diagnose H5N1 virus isolates.

In particular, a mAb designated 5A5 targets a linear epitope of H5-subtype hemagglutinin. Other mAbs, designated 5C5, 2D9, 4F8, 1C1, 3B6, 2F11, 9C1 and 3H11, target conformational epitopes of H5-subtype hemagglutinin. A mAb designated 8H12 targets a linear epitope of N1-subtype neuraminidase, and two further antibodies, designated 6C6 and 3D4, target conformational epitopes of N1-subtype neuraminidase.

Accordingly, this invention comprises a binding protein having substantially the immunological binding characteristics for a linear H5-subtype hemagglutinin epitope as those of mAb 5A5 and a binding protein having substantially the immunological binding characteristics for a linear N1-subtype neuraminidase epitope as those of mAb 8H12. The invention further comprises a binding protein having substantially the immunological binding characteristics for a conformational H5-subtype hemagglutinin epitope as those of mAb 5C5, 2D9, 4F8, 1C1, 3B6, 2F11, 9C1 and 3H11. The invention also comprises a binding protein having substantially the immunological binding characteristics for a conformational N1-subtype neuraminidase epitope as those of mAb 6C6 or 3 D4.

In a further aspect, the invention comprises a method for detecting H5 subtype AIV in a specimen which comprises detecting the binding of AIV with a mAb or binding protein having substantially the immunological binding characteristics of mAb 5A5, 5C5, 2D9, 4F8, 1C1, 3B6, 2F11, 9C1 or 3H11. The invention also comprises a method for detecting N1 subtype AIV in a specimen which comprises detecting the binding of AIV with a mAb or binding protein having substantially the immunological binding characteristics of mAb 6C6, 3D4 or 8H12. In particular, the invention relates to immunofluorescence assays, immunohistochemical assays and ELISA methods that utilize such binding proteins. The antibodies which recognize H5 subtype AIV can be used in combination with the antibody which recognizes N1 subtype AIV to detect H5N1 virus.

In another aspect, the invention relates to kits for the detection of AIV which comprise binding proteins having substantially the immunological binding characteristics of mAb 5A5, 5C5, 2D9, 4F8, 1C1, 3B6, 2F11, 9C1, 3H11, 8H12, 3D4 and/or 6C6.

The invention further relates to methods of treating subjects infected with an H5 AIV strain, such as an H5N1 AIV strain, which comprise administering to such subjects effective amounts of one or more monoclonal antibodies or binding proteins having substantially the immunological binding characteristics of mAb 5C5, 2D9, 4F8, 2F11, 9C1, 3H11, 3D4 or 6C6.

BRIEF DESCRIPTION OF THE DRAWINGS

FIGS. 1A-1D are representative IFA images comparing MDCK cells infected with AIV H5N1 against MDCK cells without virus infection. FIG. 1A is an image in which H5N1 is detected in MDCK cells. In FIG. 1B, the merge of ultraviolet light and normal light indicated the individual cells infected by virus compared to uninfected cells. There was no fluorescence signal on MDCK cells without virus infection as shown in FIG. 1C. FIG. 1D shows the merge of ultraviolet light and normal light on the same cells as in FIG. 1C.

In FIG. 2A, MDCK cells were stained with FITC fluorescence after monoclonal antibodies neutralized H5N1 virus infection. In FIG. 2B, MDCK cells were stained with FITC fluorescence without monoclonal antibody neutralization of H5N1 virus infection.

In FIG. 3A, HA1 is about 37 kD and the expressed GST-tagged HA1 is about 61 kD at the SDS-PAGE gel. GST alone is 26 kD. In FIG. 3B, Western blotting indicated recombinant HA1 reacting with mAB 5A5. Except for the major band at 61 kD, there were smaller bands which suggested degradation when GST-HA1 was expressed in *E. coli*. Lane 1, *E. coli* sample without IPTG-inducing expression; lanes 2 & 3, IPTG-inducing GST-HA1 expressed in *E. coli*; lane 4, purified GST sample.

FIGS. 4A and 4B illustrate mapping the linear epitope of mAb 5A5. FIG. 4A is a schematic diagram of the hemagglutinin protein HA1, showing the clone constructs for the expression of the different lengths of HA1 fragments and their reactivities with mAb5A5. FIG. 4B is a schematic diagram of the mutant hemagglutinin HA1 fragments, showing the clone constructs for the expression of the different mutations on the HA1 fragments and their reactivities with mAb 5A5. The sequences in FIG. 4B from top to bottom are SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13.

FIG. 5A shows the expressed recombinant N1 being detected in Sf9 cells. In FIG. 5B, the merge of ultraviolet light and normal light indicated the individual cells.

In FIG. 7A, MDCK cells were observed by microscopy after monoclonal antibodies neutralized H5N1 virus infection. In FIG. 7B, MDCK cells were observed by microscopy without monoclonal antibody neutralization of H5N1 virus infection as a CPE positive control. In FIG. 7C, MDCK cells were shown in the absence of both virus and mAb as a CPE negative control.

DETAILED DESCRIPTION OF THE INVENTION

Figures 2A, 2B:
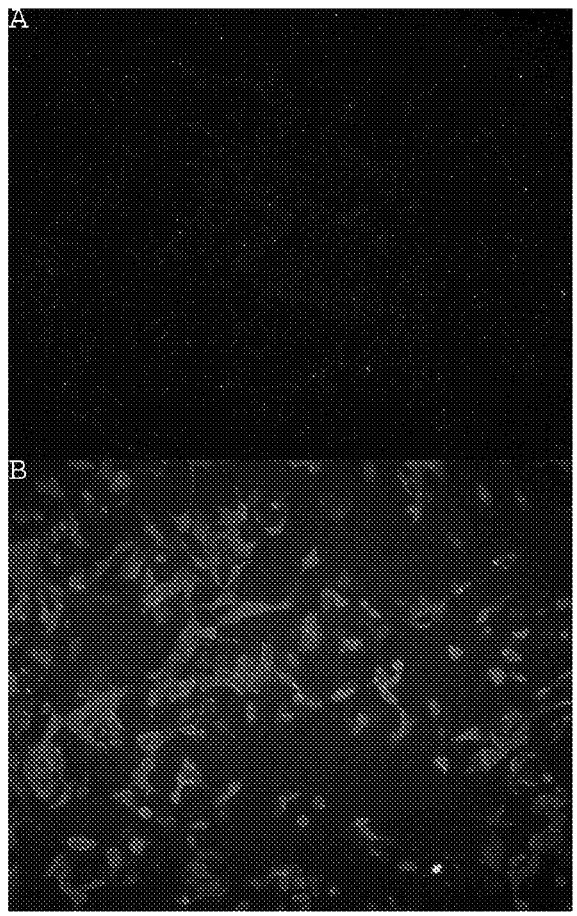
FIGS. 2A and 2B show monoclonal antibody neutralization activity of influenza virus on MDCK cells.
Figures 3A, 3B:
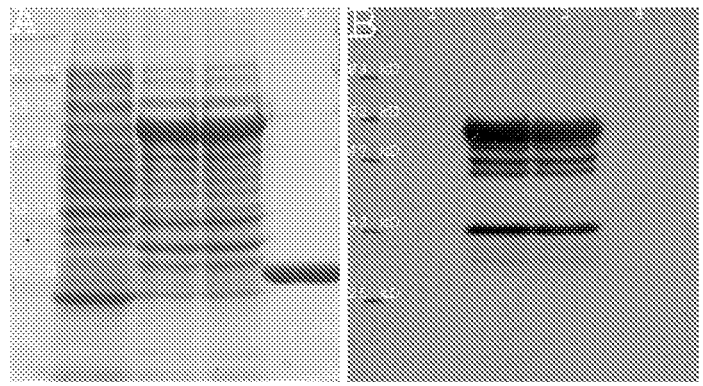
FIGS. 3A and 3B show SDS-PAGE and Western-blotting to identify the binding between mAbs and linearized recombinant HA1.

The present invention is directed to mAbs and related antigen-binding proteins that bind specifically to the AIV H5 subtype hemagglutinin glycoprotein or the AIV N1 subtype neuraminidase glycoprotein. In particular, the mAb or related antigen binding protein possesses the immunological binding characteristics of mAb 5A5 as produced by hybridoma 5A5, deposited with the American Type Culture Collection (ATCC) located at 10801 University Boulevard, Manassas, Va. 20110, USA, on Jul. 10, 2007, and assigned Accession Number PTA-8528, mAb 5C5 as produced by hybridoma 5C5, deposited with the ATCC on Jul. 10, 2007, and assigned Accession Number PTA-8529, mAb 6C6 as produced by hybridoma 6C6, deposited with the ATCC on Jul. 10, 2007, and assigned Accession Number PTA-8526, mAb 2D9 as produced by hybridoma 2D9, deposited with the ATCC on Jul. 29, 2008, and assigned Accession Number PTA-9396, mAb 4F8 as produced by hybridoma 4F8, deposited with the ATCC on Jul. 29, 2008, and assigned Accession Number PTA-9397, mAb 1C1 as produced by hybridoma 1C1, deposited with the ATCC on Jul. 29, 2008, and assigned Accession Number PTA-9398, mAb 3B6 as produced by hybridoma 3B6, deposited with the ATCC on Jul. 29, 2008, and assigned Accession Number PTA-9399, mAb 3D4 as produced by hybridoma 3D4, deposited with the ATCC on Jul. 29, 2008, and assigned Accession Number PTA-9395, mAb 8H12 as produced by hybridoma 8H12, deposited with the ATCC on Jul. 29, 2008, and assigned Accession Number PTA-9394, mAb 2F11 as produced by hybridoma 2F11, deposited with the ATCC on Jul. 16, 2008, and assigned Accession Number PTA-9373, mAb 9C1 as produced by hybridoma 9C1, deposited with the ATCC on Jul. 16, 2008, and assigned Accession Number PTA-9372, or mAb 3H11 as produced by hybridoma 3H11, deposited with the ATCC on Jul. 16, 2008, and assigned Accession Number PTA-9374. All deposits were made in accordance with the provisions of the Budapest Treaty. The invention further embodies these hybridomas and provides a continuous source of the mAbs and binding proteins of the invention.

The invention further relates to methods for the detection and diagnosis of H5 subtype AIV infection and assay kits that comprise the mAbs or binding proteins of the invention. The invention further relates to methods of treating a subject infected with an H5 or N1 AIV strain through the administration of effective amounts of one or more antibodies or related binding proteins of the invention. In particular, in this embodiment the subject is infected with an Indonesian isolate of H5N1 subtype of AIV. The antibodies of this invention also can be administered to subjects on the advent of a possible influenza pandemic as a precautionary measure. In this instance, effective amounts of antibodies to be administered are about half of the amounts used to treat H5 or N1 AIV infections.

Various terms are used herein, which have the following meanings:

The term "immunological binding characteristics" of a mAb or related binding protein, in all of its grammatical forms, refers to the specificity, affinity and cross-reactivity of the mAb or binding protein for its antigen.

The term "linear epitope" refers to a consecutive sequence of from about 4 to about 12 amino acids which form an antibody binding site. The linear epitopes of the mAbs of this invention preferably are in the region from about amino acid 260 to about amino acid 269 of the hemagglutinin protein encoded by the HA 1 viral gene. The linear epitope, in the form that binds to the mAb or binding protein, may be in a denatured protein that is substantially devoid of tertiary structure.

The term "conformational epitope" refers to a mAb or related binding protein binding site that exists in the H5-subtype hemagglutinin glycoprotein or N1-subtype neuraminidase glycoprotein in its native three-dimensional form.

The term "binding protein" refers to a protein, including those described below, that includes the antigen binding site of a mAb of the present invention or a mAb having the immunological binding characteristics of a mAb of the present invention.

The present invention advantageously provides methods for preparing monoclonal antibodies having the binding characteristics of mAb 5A5 by immunizing an animal with AIV subtype H5N2 (A/chicken/Singapore/98), preparing monoclonal antibodies having the binding characteristics of mAb 5C5 by immunizing an animal with AIV subtype H5N2 (A/chicken/Singapore/98) or preparing monoclonal antibodies having the binding characteristics of mAb 6C6 by immunizing an animal with AIV subtype H7N1 (A/chicken/Singapore/94). The invention further advantageously provides methods for preparing monoclonal antibodies having the binding characteristics of mAb 2D9 and of mAb 3B6 by immunizing an animal with AIV subtype H5N2 (A/chicken/Singapore/98). The invention also provides methods for preparing monoclonal antibodies having the binding characteristics of mAb 2F11 or 9C1 by immunizing an animal with escape mutants from parental avian influenza virus A/Vietnam/1203/2004/H5N1 with a mutation at amino acid 205 from lysine into methionine, or preparing monoclonal antibodies having the binding characteristics of mAb 3H11 by immunizing an animal with AIV subtype A/Indonesia/CDC669/2206/H5N1. The invention additionally provides methods for preparing monoclonal antibodies having the binding characteristics of mAb 3D4 and of mAb 8H12 by immunizing an animal with AIV subtype H7N1 (A/chicken/Singapore/94), and methods for preparing mAbs 4F8 and 1C1 by immunizing an animal with AIV subtype H5N2 (A/chicken/Singapore/98.

Any such antigen can be used as an immunogen to generate antibodies with the desired immunological binding characteristics. Such antibodies include, but are not limited to, monoclonal antibodies, chimeric antibodies, single chain antibodies, Fab fragments and proteins comprising the antigen binding sequence of mAb 5A5, 5C5, 2D9, 4F8, 1C1, 3B6, 2F11, 9C1, 3H11, 8H12, 6C6 or 3D4.

The mAbs of the present invention can be produced by any technique that provides for the production of antibody molecules by continuous cell lines in culture. Such methods include, but are not limited to, the hybridoma technique originally developed in 1975 by Kohler and Milstein (*Nature* 256:495-497), as well as the trioma technique, the human B-cell hybridoma technique (Kozbor et al., 1983, *Immunology Today* 4:72) and the EBV-hybridoma technique to produce human monoclonal antibodies (Cole et al., in *Monoclonal Antibodies and Cancer Therapy* Alan R. Liss, Inc., pp 77-96 (1985)). Human antibodies can be used and can be obtained by using human hybridomas (Cote et al., 1983, Proc. Nat'l. Acad. Sci. U.S.A., 80:2026-2030) or by transforming human B cells with EBV virus in vitro (Cole et al., 1985, in Monoclonal Antibodies and Cancer Therapy, Alan R. Liss, pp. 77-96). Moreover, techniques developed for the production of "chimeric antibodies" or "humanized antibodies" (Morrison et al., 1984, J. Bacteriol. 159-870; Neuberger et al., 1984, Nature 312:604-608; Takeda et al., 1985, Nature 314:452-454) by introducing sequences from a murine antibody molecule of the present invention, e.g., mAb 5C5, 5A5, 6C6, 2D9, 4F8, 1C1, 3B6, 3D4, 8H12, 2F11, 9C1 or 3H11, together with genes from a human antibody molecule of appropriate biological activity can be used. Chimeric antibodies are those that contain a human Fc portion and a murine (or other non-human) Fv portion. Humanized antibodies are those in which the murine (or other non-human) complementarity determining regions (CDR) are incorporated into a human antibody. Both chimeric and humanized antibodies are monoclonal. Such human or humanized chimeric antibodies are preferred for use in in vivo diagnosis or therapy of human diseases or disorders.

According to the invention, techniques described for the production of single chain antibodies (U.S. Pat. No. 4,946,778) can be adapted to provide single chain antibodies of the present invention. An additional embodiment of the invention utilizes the techniques described for the construction of Fab expression libraries (Huse et al., 1989, Science 246: 1275-1281) to allow rapid and easy identification of monoclonal Fab fragments with the desired specificity for the antibody of the present invention, or its derivatives, or analogs.

Antibody fragments that contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. Such antibody fragments can be generated from any of the polyclonal or monoclonal antibodies of the invention.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), immunofluorescence assays and immunoelectrophoresis assays, etc. In one embodiment, antibody binding is detected by detecting a label on the primary antibody. In another embodiment, the primary antibody is detected by detecting binding of a secondary antibody or other reagent to the primary antibody. In a further embodiment, the secondary antibody is labeled. Means are known in the art for detecting binding in an immunoassay and are within the scope of the present invention.

The foregoing antibodies can be used in methods known in the art relating to the detection or localization of the H5 or N1 subtype of AIV, e.g., Western blotting, ELISA, radioimmunoassay, immunofluorescence assay, immunohistochemical assay, and the like. The techniques disclosed herein may be applied to the qualitative and quantitative determination of the H5 subtype of AIV and to the diagnosis and surveillance of animals or humans infected with the virus.

The present invention also includes assay and test kits for the qualitative and/or quantitative determination of the H5 subtype of AIV. Such assay systems and test kits may comprise a labeled component prepared, e.g., by labeling with a radioactive atom, a fluorescent group or an enzyme, coupling a label to the mAb or related binding protein of the present invention, or to a binding partner thereof. Such assay or test kits further may comprise reagents, diluents and instructions for use, as is well known to those skilled in immunoassay techniques.

In certain embodiments of the invention, such kits will contain at least the mAb or related binding protein of the invention, means for detecting immunospecific binding of said mAb or related binding protein to AIV in a biological sample, and instructions for use, depending upon the method selected, e.g., "competitive," "sandwich," "DASP" and the like. The kits may also contain positive and negative controls. They may be configured to be used with automated analyzers or automated immunohistochemical slide staining instruments.

An assay kit of the invention may further comprise a second antibody or binding protein that can be labeled or can be provided for attachment to a solid support (or attached to a solid support). Such an antibody or binding protein may be, for example, one that binds to AIV. Such second antibodies or binding proteins may be polyclonal or monoclonal antibodies.

Monoclonal antibodies to H5-subtype hemagglutinin or N1-subtype neuraminidase protein can be prepared by immunizing animals with AIV or H5 or N1 protein or fragments thereof A preferred method for antibodies to H5-subtype hemagglutinin protein involves amplification of the H5-subtype HA1 gene followed by expression of the gene, recovery and purification of H5 subtype recombinant proteins and use of the purified proteins as immunogens. For example, H5N1 AIV is propagated by inoculation of chicken embryos with available strains of the virus, followed by isolation of the viral RNA. The HA1 gene is amplified by reverse transcriptase polymerase chain reaction (RT-PCR) and then may be cloned into a baculovirus vector that is used to express H5 proteins in insect cells. The proteins so produced then can be used to immunize mice or other suitable species for production of hybridomas. Similar procedures can be used to obtain N1 proteins for hybridoma production.

Hybridomas are screened for their ability to produce high affinity mAbs that are capable of specifically binding to H5 or N1 proteins and distinguish them from other AIV subtypes. In accordance with the invention, it has been found that antibodies with virus neutralization ability are able to recognize conformational epitopes in the H5-subtype hemagglutinin proteins. This finding resulted from the generation of virus escape mutants in the presence of each neutralizing mAb after 1-2 rounds of selection in Madin-Darby canine kidney (MDCK) cells or chicken embryos. The HA' gene was cloned from these neutralization escape mutants by RT-PCR and sequenced to identify point mutations. In this panel of antibodies, neutralization epitopes were found in mAbs 5C5, 2F11, 9C1 and 3H11. Neutralization-escape ability was confirmed using hemagglutination inhibition assays.

HA1 contains 338 amino acids, including the signal peptide of 16 amino acids. To study the distribution of linear epitopes on the protein, truncated and mutated fragments are advantageously tested for binding with mAbs, e.g., by Western blot or a similar technique. Linear epitopes may be identified that are binding targets for mAbs that give a good performance in detecting denatured H5 subtype protein, such as that occurring in formalin-fixed tissue, using immunohistochemical staining methods. Mapping of the H5 subtype mAbs in this manner provides a platform for further study and a more effective clinical diagnosis of the infectious H5N1 AIV.

The present invention also has provided a better understanding of the antigenic structure of AIV H5 hemagglutinin and N1 neuraminidase molecules. The mAbs and related binding proteins of the invention provide a means for detecting this highly pathogenic virus in frozen sections and biological specimens.

The ability to detect viruses in paraffin sections is of great importance. Under most circumstances, AIV antigens in infected tissue sections are destroyed by the fixation process. Formalin and ethanol have the potential to remove the lipid envelope and envelope glycoproteins, including hemagglutinin, thus increasing the difficulties in viral antigen detection. Therefore, this form of diagnosis has the potential to provide a safer and more precise diagnosis of AIV-infected animal and human tissues.

As illustrated in the examples below, mAb 5A5 is highly efficacious and sensitive to viral antigen in formalin-fixed tissues. This antibody allows infected regions to be easily visualized under a light microscope. Antibody 5A5 does not have hemagglutinin inhibition or viral neutralization activities; however, it exhibits positive results in immunofluorescence assay and in Western blot analysis, strong bands that correspond to the recombinant H5N1-HA protein (MW 36 kDa) are observed.

MAb 8H12 also is highly efficacious and sensitive to viral antigen in formalin-fixed tissues. This antibody also allows infected regions to be easily visualized under a light microscope.

In contrast, mAbs 5C5, 2D9, 4F8, 1C1, 3B6, 6C6, 3D4, 2F11, 9C1 and 3H11 are highly efficacious on frozen tissue sections but do not detect antigen in formalin-fixed tissues. These results imply that the two groups of mAbs react with different viral epitopes. Through epitope mapping, mAbs 5A5 and 8H12 were determined to target linear epitopes. They could only detect viral antigens when the tissues were subjected to intensive heat treatment. Under such harsh antigen retrieval methods, surface proteins of the virus were destroyed and left nucleoprotein of the virus exposed. Therefore, mAbs that target linear epitopes did not work as well on frozen tissue sections.

Monoclonal antibodies 5C5, 2D9, 4F8, 1C1, 3B6, 6C6, 3D4, 2F11, 9C1 and 3H11 were determined to target conformational epitopes of the H5N1 virus. Epitope mapping was used to make this determination for mAb 5C5, 2D9, 4F8, 2F11, 9C1 and 3H11; the determination of mAb 6C6 and 3D4 was made on the basis that the antibodies could not recognize denatured neuraminidase from SDS-PAGE. These antibodies were able to bind and to recognize viral antigens without prior treatments of the tissue sections.

This invention provides convenient, highly specific and sensitive means for detecting H5 and N1 subtypes of AIV. One such means is the ELISA format. In a preferred embodiment mAbs 5A5, 5C5, 2D9, 4F8, 1C1, 3B6, 2F11, 9C1 and 3H11, alone or in combination, are used as capture antibodies. It has been found that the combination of mAbs 5A5 and 5C5 provides high optical density readings in detection of H5-subtype AIVs in comparison to either antibody alone or in other combinations described herein. While not bound by theory, a possible explanation of these results is that the two antibodies react with different epitopes on the HA1 protein and are of different antibody subclasses, therefore providing multiple binding sites.

If the antibodies are used alone, the selected antibody can be used, for example, as a capture antibody and the same antibody conjugated with horseradish peroxidase (HRP) can be used as the detecting antibody. The 6C6, 3D4 and 8H12 antibodies can be used similarly as capture antibodies for the detection of N1 subtype strains of AIV.

Monoclonal antibodies against conformational epitopes maintain important biological functions, such as hemagglutination inhibition and neutralization activity, while mAbs against linear epitopes also are advantageous for diagnostic uses. Therefore, the application of mAb 5A5 and of mAbs 5C5, 2D9, 4F8, 1C1, 3B6, 2F11, 9C1 and 3H11, which are against linear and conformational epitopes, respectively, might contribute greatly to the high sensitivity of ELISA procedures. Similarly, the application of mAb 8H12 and of mAbs 6C6 and 3D4, which are against linear and conformational epitopes, respectively, of N-1 neuraminidase may contribute greatly to the high sensitivity of ELISA procedures. The approach of using two mAbs also may be used to develop other immunological methods to detect H5 and N1 viruses, such as, for example, by dot-blot and in situ hybridization formats.

A preferred ELISA test of this invention is able to detect HA antigen from H5N1 AIV infecting poultry and humans in Indonesia, indicating the utility of the invention for detecting both avian and human H5N1 infections.

The H5-subtype and N1-subtype mAbs of this invention have advantages over other current methodologies as diagnostic tools. First, mAbs 5A5, 5C5, 2D9, 4F8, 1C1, 3B6, 2F11, 9C1 and 3H11 are highly specific for the highly infectious H5-subtype AIV, and all but the 9C1 mAb have been shown to recognize all, or nearly all, known Indonesian strains of H5N1. In addition, mAbs 6C6, 3D4 and 8H12 are highly specific for N1-subtype AIV and can be used to diagnose infections of N1 subtype viruses, including all, or nearly all, known Indonesian strains of H5N1. Such highly specific monoclonal antibodies represent a breakthrough in the field of avian influenza diagnosis. Prior to the present invention, no monoclonal antibody had been reported that could detect all, or nearly all, Indonesian H5N1 viruses. All but one of the monoclonal antibodies of the present invention have been shown to recognize all, or essentially all, of the H5N1 viruses collected in Indonesia within the last two years. MAb 6C6, 3D4 or 8H12 can be used in combination (together or sequentially) with mAb 5A5, 5C5, 2D9, 4F8, 1C1, 3B6, 2F11 or 3H11 to pinpoint that a particular isolate is an H5N1 isolate. Additionally, the ability of the mAbs to detect and accurately localize H5 viral antigen in infected formalin-fixed tissue as well as in serological tests, such as HI and IFA, represent a distinct advantage. Furthermore, these mAbs provide a safe and convenient diagnostic approach for the detection of H5 and N1 AIV infections. Frozen section slides can be cryogenically stored for long periods of time and facilitate further diagnosis and surveillance of infections. The antibodies of this invention thus are useful for the diagnosis of H5N1 infections. As discussed below, mAbs of this invention also are useful for treatment of H5N1 infections. Accordingly, mAbs of this invention will be very useful tools in restraining a potential flu pandemic. Another embodiment of the invention relates to neutralization escape mutants of H5 avian influenza. The term "neutralization escape mutant" refers to a mutant virus raised by point mutations in the genes encoding hemagglutinin which caused antigenic drift in the H5 or N1 virus and affect neutralization epitopes. A neutralization escape mutant can evade neutralization by certain monoclonal antibodies that are effective in neutralizing its parent virus. In manual screening for escape mutants, a parental virus is incubated with a certain neutralization antibody and inoculated into a host, such as MDCK cells or chicken embryos. After 2-3 rounds of screening, the escape mutant for the neutralization mAb is cloned and subjected to HA1 gene sequencing. The mutated amino acid is determined by alignment with the parental virus sequence, and the mutated site indicates exactly one of the amino acids comprising the neutralization epitope recognized by the neutralization mAb.

In the present invention, 5C5 escape mutants arise from A/Indonesia/CDC669/H5N1 AIV by the 5C5 neutralization monoclonal antibody. The mutation sites are listed in Example 3, Table 4, below. 2F11 escape mutants arise from A/Vietnam/1203/2004/H5N1 by the 2F11 neutralization monoclonal antibody. 9C1 escape mutants arise from the K189M mutant of A/Vietnam/1203/2004/H5N1 by the 9C1 neutralization monoclonal antibody. In addition 3H11, 2F9 and 9C1 escape mutants arise from A/Indonesia/CDC669/2006/H5N1. The mutation sites are listed in Example 3, Table 4, below.

Neutralization escape mutants are different from their parental virus in that they no longer can be recognized by certain neutralization antibodies which specifically bind to the parent virus. In view of this, these mutants can be used to immunize mice for new monoclonal antibody production in accordance with the teachings above. Among the new mAbs, a monoclonal antibody which exactly recognizes the mutated epitope can be screened out which then can be used to provide complementary surveillance to avian influenza viruses other than the parental virus. By repeating this process through several generations, further escape mutants can be found and further neutralizing antibodies obtained. These antibodies can be used in the methods of the present invention.

In a further embodiment of the invention, antibodies and related binding proteins of the invention can be administered to treat subjects suffering from an H5 AIV infection, particularly an infection from an H5N1 subtype of AIV. Antibodies and related binding proteins of the invention also can be administered to subjects as a preventive measure in the event of an influenza pandemic or threatened pandemic. The antibodies and related binding proteins can be administered in a single dose or in repeated administrations, optionally in a slow release form. Administration can be made by any means that enables the antibody to reach its site of action in the body of the subject being treated, e.g., intravenously, intramuscularly, intradermally, orally or nasally. Typically, the antibody is administered in a pharmaceutically acceptable diluent or carrier, such as a sterile aqueous solution, and the composition can further comprise one or more stabilizers, adjuvants, solubilizers, buffers, etc. The exact method of administration, composition and particular dosage will be determined and adjusted at the time of therapy, depending upon the individual needs of the subject, taking into account such factors as the subject's age, weight, general health, and the nature and extent of his or her symptoms, as well as the frequency of treatment to be given. Generally, the dosage of antibody administered is within the range of about 0.1 mg/kg to about 1 mg/kg body weight when the antibody is administered to treat patients suffering from an H5 AIV infection. Typically, the dosage is reduced by about half, i.e. to within the range of about 0.05 mg/kg to about 0.5 mg/kg body weight, when administered as a preventive measure.

A single neutralizing antibody or binding protein of the invention can be administered for therapeutic purposes or a combination of two or more can be administered. If antibodies to one or more generations of neutralization escape mutants have been produced, such antibodies and an antibody of the invention described above can be administered as therapeutic antibody "cocktails." Preferred antibodies for use as a therapeutic agent include the 5C5, 2D9, 2F11, 9C1, 3H11 and 4F8 mAbs.

The following examples are provided to illustrate a preferred mode of practicing the invention. The invention is not limited to the details of the examples, but is commensurate with the full scope of the appended claims.

Example 1

Production of Hybridomas

All live wild type H5N1 influenza viruses, except H5N1/PR8, were obtained from Indonesia. H5N1/PR8 was obtained from the Center for Disease Control (USA). It is a non-pathogenic recombinant virus that contains the HA and NA genes of an AIV H5N1 virus that infected a human in Vietnam (A/Vietnam/1203/2004). H5N2 (A/chicken/Singapore/98) and H7N1 (A/chicken/Singapore/94) were obtained from Agri-Food & Veterinary Authority (AVA) of Singapore. These virus stocks were used to infect 9 and 11 day old embryonated chicken eggs (Chew's Poultry Farm, Singapore) and allowed to replicate for two generations. Then, allantoic fluid was drawn and viral titer was determined using hemagglutinin assay (HA). Inactivated H5N1 (A/goose/guangdong/97) was used for RNA extraction to amplify HA1 gene by RT-PCR. Madin Darby kidney cells (MDCK, ATCC CCL34) cells were grown in DMEM media with 10% FBS at 37° C. with 5% $CO_2$.

Purification of the viruses was performed by centrifugation of virus-containing allantoic fluids at 10,000 rpm for 30 minutes to remove debris, followed by ultracentrifugation of the supernatant at 40,000 rpm for 3 hours. The virus pellet was suspended in PBS.

Monoclonal antibodies were purified from clarified fluids using protein A affinity column (Sigma Aldrich; St. Louis, Mo., USA) and Immunopure® IgM purification kit (Pierce Biotechnology; Rockford, Ill., USA) in accordance with manufacturer's instructions. The antibody concentrations were measured by using an ND-1000 spectrophotometer (NanoDrop Technologies; Wilmington, Del., USA).

BALB/c mice were immunized with inactivated avian influenza virus of H5N2(A/chicken/Singapore/98) or H7N1 (A/chicken/Singapore/94) with the oil adjuvant Montanide ISA563 (Seppic, France) in a volume of 0.2 ml. Intraperitoneal injections were delivered on days 0, 14, 28 and 42. Splenocytes from immunized mice and myeloma cells (SP2/0) were collected and fused as described by De St. Groth and Scheidigger to produce hybridomas (16). After selection with hypoxanthine-aminopterin-thymidine (HAT) medium, culture media from the hybridomas showing significant growth after 14 days were tested for the presence of specific antibodies against H5N1/PR8-infected MDCK cells by immunofluorescence assay (IFA). Selected hybridomas were cloned by limiting dilution, re-identified, cloned a second time, and retested by IFA. Once established, the hybridoma line was propagated in tissue culture and frozen in liquid N2 for future use.

Hybridomas from which each of the specific monoclonal antibodies of the present invention was obtained were made in accordance with these general procedures.

Example 2

Screening of mAbs by IFA

Immunofluorescence assay was used to verify the interaction between an antibody and the antigen target. MDCK cells which had been infected with influenza virus (H5N2 (A/chicken/Singapore/98) or H7N1 (A/chicken/Singapore/94) overnight were rinsed with PBS-T (0.05% Tween-20 in PBS, pH 7.4) in 96 well plates. The cells were fixed by incubating them in pre-cooled 100% ethanol for 10 minutes. The cells were washed in PBS-T 3 times, then incubated in 1% BSA, PBS-T for 30 minutes to block unspecific binding of the antibodies. They then were incubated with 100 µL of hybridoma culture fluid in wells of 96-well plates for 2 hours at room temperature or overnight at 4° C. The cells were washed with PBS-T and incubated with secondary antibodies, fluorescently labeled goat/rabbit anti-mouse antibodies (DakoCytomation, USA), at a dilution of 1:100 in 1% BSA, PBS-T, for 60 minutes at room temperature. The wells were washed with PBS-T. The PBS-T was discarded and 50% glycerol in PBS was added. Fluorescence signals were checked under a microscope with ultraviolet light.

Uninfected MDCK cells were used as negative controls. Serum from a mouse immunized with inactivated H5N1 virus was used as positive antibody control. By comparing MDCK cells incubated with the respective hybridoma supernatants with the controls, the hybridoma supernatants which gave positive staining were selected for cloning by limiting dilution. Stable mAb producing hybridomas were obtained by this procedure.

Antibodies designated mAb 5A5, 5C5, 2D9, 4F8, 1C1, 2F11 and 3B6 were found to bind to H5N1 hemagglutinin from all 25 isolates from Indonesia, as well as to H5N1/PR8 and H5N2. MAb 3H11 binds to hemagglutinin from almost all of the 25 Indonesian isolates, but not to H5N1/PR8 and H5N2. MAbs 6C6, 3D4 and 8H12 were found to bind to neuraminidase from all of the H5N1 isolates from Indonesia, as well as H5N1/PR8 and H7N1. MAb 9C1 has been shown to bind to a specific Indonesian strain of H5N1; as this antibody was generated from an escape mutant of a particular strain, it specifically binds to strains of AIV Clade 1 with a non-lysine as the $205^{th}$ amino acid of H5. This unique property of the 9C1 mAb enables it to combine with other 205-lysine specific mAbs in therapeutic applications without the concerns of virus evasion.

The AIV strains which react with the mAbs of this invention are listed in Table 1 below.

Representative IFA images are shown in FIG. 1.

TABLE 1

| MAbs (target) | 5A5 (H5) | 5C5 (H5) | 6C6 (N1), 3D4 (N1) | 1C1 (H5), 3B6 (H5) | 2D9 (H5), 4F8 (H5) | 8H12 (N1) | 2F11 (H5) | 3H11 (H5) | 9C1 (H5) |
|---|---|---|---|---|---|---|---|---|---|
| A/Indonesia/chicken/60/2006(H5N1) | + | + | + | + | + | + | + | + | N.T. |
| A/Indonesia/CDC7/2005(H5N1) | + | + | + | + | + | + | + | + | N.T. |
| A/Indonesia/CDC326/2006(H5N1) | + | + | + | + | + | + | + | + | N.T. |
| A/Indonesia/CDC329/2006(H5N1) | + | + | + | + | + | + | + | + | N.T. |
| A/Indonesia/CDC370/2006(H5N1) | + | + | + | + | + | + | + | + | N.T. |
| A/Indonesia/CDC390/2006(H5N1) | + | + | + | + | + | + | + | + | N.T. |
| A/Indonesia/CDC523/2006(H5N1) | + | + | + | + | + | + | + | − | N.T. |
| A/Indonesia/CDC594/2006(H5N1) | + | + | + | + | + | + | + | − | − |
| A/Indonesia/CDC623/2006(H5N1) | + | + | + | + | + | + | + | + | N.T. |
| A/Indonesia/CDC644/2006(H5N1) | + | + | + | + | + | + | + | + | N.T. |
| A/Indonesia/CDC669/2006(H5N1) | + | + | + | + | + | + | + | + | + |
| A/Indonesia/TLL001/2006(H5N1) | + | + | + | + | + | + | + | + | N.T. |
| A/Indonesia/TLL002/2006(H5N1) | + | + | + | + | + | + | + | + | N.T. |
| A/Indonesia/TLL003/2006(H5N1) | + | + | + | + | + | + | + | + | N.T. |
| A/Indonesia/TLL004/2006(H5N1) | + | + | + | + | + | + | + | + | N.T. |
| A/Indonesia/TLL005/2006(H5N1) | + | + | + | + | + | + | + | + | N.T. |
| A/Indonesia/TLL006/2006(H5N1) | + | + | + | + | + | + | + | + | N.T. |
| A/Indonesia/TLL007/2006(H5N1) | + | + | + | + | + | + | + | + | N.T. |
| A/Indonesia/TLL008/2006(H5N1) | + | + | + | + | + | + | + | + | N.T. |
| A/Indonesia/TLL009/2006(H5N1) | + | + | + | + | + | + | + | + | N.T. |
| A/Indonesia/TLL010/2006(H5N1) | + | + | + | + | + | + | + | + | N.T. |

TABLE 1-continued

| MAbs (target) | 5A5 (H5) | 5C5 (H5) | 6C6 (N1), 3D4 (N1) | 1C1 (H5), 3B6 (H5) | 2D9 (H5), 4F8 (H5) | 8H12 (N1) | 2F11 (H5) | 3H11 (H5) | 9C1 (H5) |
|---|---|---|---|---|---|---|---|---|---|
| A/Indonesia/ TLL011/ 2006(H5N1) | + | + | + | + | + | + | + | + | N.T. |
| A/Indonesia/ TLL012/ 2006(H5N1) | + | + | + | + | + | + | + | + | N.T. |
| A/Indonesia/ TLL013/ 2006(H5N1) | + | + | + | + | + | + | + | + | N.T. |
| H5N1/PR8 | + | + | + | + | + | + | + | − | − |
| A/chicken/ Singapore/ 98(H5N2) | + | + | − | + | + | − | + | − | − |
| (H7N1) | − | − | + | − | − | + | − | − | − |
| (H3N2) | − | − | − | − | − | − | − | − | − |
| (H9N2) | − | − | − | − | − | − | − | − | − |
| (H10N5) | − | − | − | − | − | − | − | − | − |

Note:
"+" means positive,
"−" indicates negative,
"N.T." means the test has not been done.

Example 3

Characterization of H5- and N1-Subtype mAbs

Isotyping of mAbs.
Isotyping was performed using a mouse mAb isotyping kit (Amersham Bioscience, England) following the protocol supplied with the kit (data not shown). MAbs 5A5, 6C6, 2D9, 4F8, 1C1, 3B6, 3D4, 8H12, 9C1 and 3H11 all were determined to be IgG1. MAb 5C5 was determined to be IgG2a, and mAb 2F11 was determined to be IgM.

Hemagglutination-Inhibition Test (HI).
A constant amount of hemagglutinating (HA) antigen was added to each well in a microtiter plate (NUNC). The testing antibody then was placed in the first well and serially diluted. The plates were incubated for one hour and then chicken red blood cells (RBC) were added to each well. If antibody was present in the test serum the RBCs would not agglutinate with the HA antigen. HI negative wells would have a diffuse sheet of agglutinated RBCs covering the bottom of the well. HI positive wells would have a well-circumscribed button of unagglutinated RBCs.

MAbs 5C5, 2D9, 2F11 and 4F8 in culture fluid had HI activity from 16 to 64 with all Indonesian H5N1 isolates and with H5N1/PR8. MAbs 9C1 and 3H11 had HI activity with some of these Indonesian H5N1 isolates. On the basis of the antigenic epitope targeted by mAb 3H11, that antibody is able to specifically and sensitively recognize H strains in Clade 2.1.3. MAbs 5A5, 1C1 and 3B6 had no HI activity.

Virus Micro-Neutralization Assay.
MDCK cells were used for determination of 50% tissue culture infections dosage (TCID50). Antibodies with two-fold serial dilutions were added to 96-well cell culture plates. The diluted antibodies were mixed with an equal volume of diluent containing influenza virus at 100 $TCIS_{50}$/well. After a 2-hour incubation at 37° C. in a 5% $CO_2$ humidified atmosphere, 100 µl of MDCK cells at $1.5 \times 10^5$/ml were added to each well. The plates were incubated for 18 hours at 37° C. and 5% $CO_2$. The monolayers were washed with PBS and fixed in 100% ethanol for 10 minutes. The presence of viral protein was detected by ELISA with mouse sera against the influenza H5N1.

The ELISA was performed at room temperature. The fixed plates were washed 3 times with PBS-T (PBS containing 0.05% Tween 20). The mouse sera antibody diluted 1/500 in PBS-T containing 1% bovine serum albumin was added to each well and incubated at room temperature for 1 hour. The plates were washed four times in wash buffer and 100 µl of horseradish peroxidase-labeled goat anti-mouse immunoglobulin (DakoCytomation, USA) diluted 1/2000 were added to each well. The plates were incubated for 1 hour at room temperature and then washed six times with wash buffer. One hundred microliters of freshly prepared substrate (10 mg of o-phenylenediamine dihydrochloride per 20 ml of 0.05M phosphate citrate buffer, pH 5.0, containing 0.03% sodium perborate) were added to each well and the plates were incubated at room temperature for approximately 5 minutes. The reaction was stopped with 50 µL of 2N sulfuric acid. The absorbance was measured at 490 nm ($A_{490}$) with an automated plate spectrophotometer (Mitenyi Biotec).

TABLE 2

| | MAb + Virus | | Virus | |
|---|---|---|---|---|
| MAb5C5 | #1 | #2 | #3 | #4 |
| A/Indonesia/chicken/60(H5N1) | 0.637 | 0.664 | 1.187 | 1.213 |
| A/Indonesia/CDC7/2005(H5N1) | 0.4 | 0.404 | 1.613 | 1.468 |
| A/Indonesia/CDC370/2006(H5N1) | 0.379 | 0.376 | 1.738 | 1.727 |
| A/Indonesia/CDC594/2006(H5N1) | 0.417 | 0.361 | 1.032 | 0.968 |
| A/Indonesia/CDC623/2006(H5N1) | 0.311 | 0.306 | 1.416 | 1.491 |
| A/Indonesia/TLL006/2006(H5N1) | 0.261 | 0.259 | 1.775 | 1.626 |
| A/Indonesia/TLL007/2006(H5N1) | 0.637 | 0.598 | 1.266 | 1.224 |
| A/Indonesia/TLL008/2006(H5N1) | 0.592 | 0.574 | 1.557 | 1.575 |
| A/Indonesia/TLL013/2006(H5N1) | 0.548 | 0.539 | 0.974 | 1.034 |
| H5N1/PR8 | 0.224 | 0.208 | 0.532 | 0.588 |
| DMEM Medium | 0.089 | 0.09 | 0.079 | 0.074 |

As shown in Table 2, mAb 5C5 neutralized H5N1 isolates on infected MDCK cells. In the presence of the monoclonal antibody, the ELISA reading results were reduced to about one half of those obtained from the cells in the absence of antibody, indicating that the virus particles had been neutralized.

Because the ELISA reading had a high background while IFA is visible, the neutralization tests were done by the detect method of IFA on MDCK cells to confirm the neutralization ability of the monoclonal antibody. MAb 5C5 could neutralize the infection of all H5N1 isolates. These results were consistent with the IFA test results.

FIGS. 2A and 2B illustrate mAb neutralization activity on MDCK cells infected with AIV. FIGS. 2A and 2B show MDCK cells stained with FITC fluorescence subsequent to mAB neutralization of virus infection and absent mAb neutralization, respectively.

Titration of Virus Neutralization on MDCK Cells and in Chicken Embryos.

MDCK cells and 10-day old embryos were used for determination of 50% tissue culture infections dosage ($TCID_{50}$) and 50% embryo infectious dosage ($EID_{50}$), respectively. MDCK cells ($2 \times 10^4$/ml) were allowed to grow to 70%-90% confluence.

Chicken embryos were infected with the respective viruses, using a series of dilution factors from $10^{-1}$ to $10^{-8}$, and the subsequent allantoic fluids were tested for $TCID_{50}$ and $EID_{50}$. The viruses then were used to infect both MDCK cells at their exponential phase (highest sensitivity to virus infection) and 10-day old chicken embryos. Uninfected MDCK cells and allantoic fluid were used as negative controls. The cells were incubated at 35° C. and CPE was observed. Using the Reed and Muench mathematical technique (17), the infectivity titer was expressed as $TCID_{50}$/100 µl and $1000 EID_{50}$/200 µl and the respective viruses were each diluted to having 100 $TCID_{50}$ and 500 $EID_{50}$ in 50 µl and 100 µl, respectively.

Serially diluted mAb 5C5 was able to neutralize the final concentration of 100 $TCID_{50}$ and 500 $EID_{50}$ of virus (e.g. A/Indonesia/DCD669/H5N1) in infected MDCK cells and embryos. See Table 3. The numbers in Table 3 reflect the highest dilution ratio of H5N1 viruses at which the mAb was still able to detect and neutralize the virus at a final concentration of 100 $TCID_{50}$ and 500 $EID_{50}$ of viruses in infected MDCK cells and chicken embryos.

TABLE 3

|  | 5C5 |
| --- | --- |
| MDCK | 160 |
| Embryo | 40 |

Figure 7A:
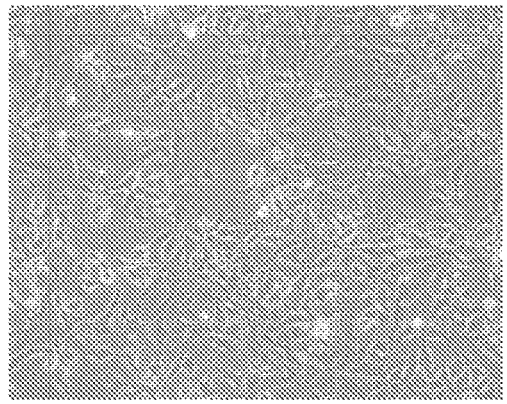
FIGS. 7A, 7B and 7C show monoclonal antibody neutralization activity of influenza virus on MDCK cells.
Figure 7B:
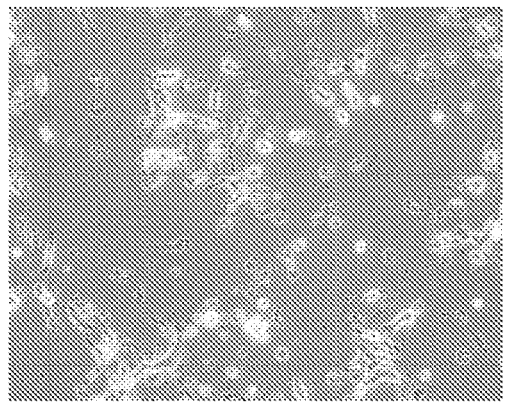
Figure 7C:
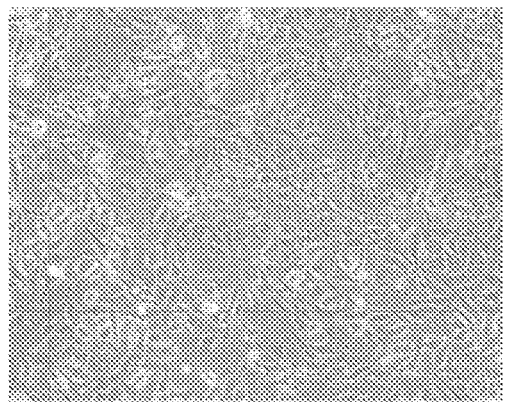

MAbs 2D9, 3H11, 9C1, 2F11 and 4F8 are similar to mAb 5C5, recognizing conformational epitopes of H5 and having the ability to neutralize influenza virus infection on MDCK cells. Virus neutralization and determination of the 50% tissue culture infections dosage (TCID50) were carried out as described above for mAb 5C5. MDCK cells (2×104/ml) were allowed to grow to 70%-90% confluence. The virus A/Indonesia/CDC669/H5N1 then was used to infect MDCK cells at their exponential phase (highest sensitivity to virus infection). Uninfected MDCK cells were used as cytopathic effect (CPE) negative control and infected cells as CPE positive control. The cells were incubated at 35 degrees C. and CPE was checked daily. The results are shown in FIGS. 7A, 7B and 7C. In the presence of the monoclonal antibody, MDCK cells did not show CPE, thus indicating that the mAb has neutralizing ability.

MAbs 1C1 and 3B6, which also recognize conformational epitopes of H5, were shown through a similar analysis to lack the ability to neutralize influenza virus infection on MDCK cells.

Epitope Characteristics and Mapping.

1a. Mapping Linear Epitope of mAb 5A5.

Sodium dodecyl sulfate-polyacrylamide gel electrophoresis (SDS-PAGE) and Western blotting were used to identify and locate linear epitopes of monoclonal antibody 5A5, as shown in FIGS. 4A and 4B. SDS-PAGE and Western blotting were performed as described by Ausubel et al. (18). The GST-tagged recombinant HA1 from H5N1 was expressed and subjected to 10% SDS-PAGE. Recombinant HA1 is about 32 kD, and the expressed GST-tagged HA1 is about 57 kD. The protein samples were prepared by mixing protein sample with sample buffer and heated at 100° C. for 5 minutes. After a brief spin, whole-cell lysate was loaded. Proteins separated by SDS-PAGE were visualized by staining with Coomassie Blue (0.25% Coomassie Brilliant Blue R-250, 40% methanol and 10% glacial acetic acid) for 30 minutes and then destained overnight in destaining solution (40% methanol and 10% glacial acetic acid). For Western blots, proteins were transferred from gel to a nitrocellulose membrane using a Transblot Cell (Bio-Rad). After electrotransfer, the membrane was blocked with 5% non-fat milk (Bio-Rad) in PBS-T and processed in the same manner as the dot blots above. The membrane was blocked with 5% non-fat milk (Bio-Rad, Canada) in PBS with 0.05% Tween-20 (PBS-t) for 60 minutes. After blocking, undiluted hybridoma culture fluid containing mAbs was incubated with the membrane for 60 minutes, washed with PBS-T and then incubated with goat anti-mouse horseradish peroxidase-conjugated antibodies (1:2000 dilution) (DakoCytomation) for 60 minutes. The membrane was washed and then developed with ECL Western blotting detection reagent (Amersham Biosciences) and exposed to KODAK Scientific imaging film (KODAK BioMAX MS, USA).

MAb 5A5 reacted with denatured recombinant HAL which suggested the epitope of MAb 5A5 was linear. MAb 5C5 could not react with denatured recombinant HA1, which indicated that the epitope of this mAb is conformational.

To map the linear epitope of mAb 5A5, the HA1 of H5 subtype was dissected into 3 overlapping fragments by PCR and expressed as a 6-histidine-tag fusion protein. By Western blotting with mAb5A5, the epitope was found primarily in the overlapping region of fragment B and C (aa 201-271). Five truncated fragments were designed for further mapping (FIG. 4A) by Western blotting, and the epitope was narrowed down between amino acid 258 and 271. To find out the exact amino acid sequence of the linear epitope, nine mutants with individual amino acid point mutations were constructed. Each of amino acids 259-264 and 268-271 on HAL with the exception of amino acid 269, was changed into alanine individually by certain primers; amino acid 269 was changed from alanine to proline (FIG. 4B). From the results of the Western blotting shown in FIG. 4B, the sequence of the linear epitope targeted by mAb5A5 is amino acids 260-269, AsnGlyAsnPheIleAla-ProGluTyrAla (NGNFIAPEYA), on hemagglutinin of subtype 5H.

1b. Determination of Linear Epitope of mAb 8H12.

Sodium dodecyl sulfate-polyacrylamide gel electrophoresis (SDS-PAGE) and Western Blotting were used to verify linear epitope of mAb 8H12 according to the procedures set forth in section 1a. above for mAb 5A5. The MBP-tagged recombinant NA1 from H5N1 was expressed and subjected to 10% SDS-PAGE. Recombinant NA1 is about 36 kD, and the expressed MBP-tagged NA1 is approximately 82 kD. MAb 8H12 reacted with denatured NA1, which suggested that the epitope of the antibody was linear.

1c. Determination of Conformational Epitopes 2D9, 4F8, 1C1, 3B6, 2F11, 9C1 and 3H11.

The procedures of section 1a. above were carried out using each of mAbs 2D9, 4F8, 3B6, 1C1, 2F11, 9C1 and 3H11. None of these antibodies reacted with denatured HAL which indicated that the epitopes of these mAbs are conformational.

1d. Determination of Conformational Epitopes of mAb 6C6 and 3D4.

The procedures of section 1b. above were carried out using mAb 6C6 and 3D4. Neither antibody reacted with denatured NA1, which indicated that the epitopes of these two antibodies are conformational.

2. Selection of Escape Mutant and Conformational/Neutralizing Epitope Mapping of H5 Subtype mAbs.

Serial 10-fold dilution of parental virus A/Indonesia/CDC669/2006(H5N1) was mixed with an equal volume of mAb. After incubation of 1 hour at room temperature, the mixture was inoculated onto a monolayer of MDCK cells in DMEM medium containing 200 μg/ml TPCK-treated trypsin (Sigma) and 0.001% DEAE-dextran (Sigma). After 7 days at 35° C., the virus supernatant was collected and subject to further selection. Escape mutants also were generated using an alternative method in which the parental strain was incubated with an excess of mAb for at least 0.5 hours at room temperature. The mixture then was inoculated into 10-day old chicken embryos. After 2 or 3 days at 35° C., the virus supernatant was collected and subject to further selection. Following either method, the escape mutant was cloned and collected for RNA extraction. The point mutation responsible for the resistance to mAb neutralization was determined by sequence alignment with the parental virus. The ability of this mutation to allow the mutant virus to escape mAb neutralization was verified by neutralization assay and hemagglutinin inhibition assay.

Several escape mutants were selected using neutralized mAb 5C5. The escape mutants were cloned and collected for RNA extraction. According to the sequence, the point mutation happens on nucleotides 524, 503 and 602, respectively, on the HA sequence (sequence available in GenBank; GenBank Accession # CY014481; GenBank GI #113497155). Nucleotide 524 "C" changes into "T," which results in mutation on amino acid 175 from threonine into isoleucine. Nucleotide 503 "A" changes into "T," which results in mutation on amino acid 168 from lysine into isoleucine. Nucleotide 602 "C" changes into "A," which results in mutation on amino acid 201 from alanine into glutamic acid. Such mutations enable the mutant virus to escape antibody neutralization from mAb 5C5, which was verified with neutralization assays and hemagglutinin inhibition assay. This result indicated the mAb 5C5 targets the epitope containing amino acids 168, 175 and 201 on hemagglutinin. The results are indicated in Table 4, which shows the location of the mAb neutralization epitope on the hemagglutinin molecule of AIV (A/Indonesia/CDC669/H5N1).

Point mutations for other mAbs were determined similarly, as shown in Table 4.

TABLE 4

| Parental Virus | Mab | Nucleotide | Nucleotide Change | Amino acid | Amino acid Change |
|---|---|---|---|---|---|
| CDC669 | 5C5 | 524 | C to T | 175 | Thr to Ile |
| CDC669 | | 503 | A to T | 168 | Lys to Ile |
| | | 602 | C to A | 201 | Ala to Glu |
| | 3H11 | 464 | G to A | 155 | Gly to Glu |
| | 2F11 | 772 | G to A | 258 | Gly to Lys |
| | 2F11 | 628 | C to T | 210 | Pro to Ser |
| | 9C1 | 599 | C to A | 200 | Ala to Glu |
| | 2D9 | 717 | T to A | 239 | Ser to Arg |

TABLE 4-continued

| Parental Virus | Mab | Nucleotide | Nucleotide Change | Amino acid | Amino acid Change |
|---|---|---|---|---|---|
| | | 613 | A to T | 205 | Arg to Trp |
| | | 717 | T to A | 239 | Ser to Arg |
| | | 470 | C to T | 157 | Pro to Leu |
| | | 717 | T to A | 239 | Ser to Arg |
| | 4F8 | 512 | G to T | 171 | Ser to Ile |
| | | 715 | A to C | 239 | Ser to Arg |
| | | 512 | G to T | 171 | Ser to Ile |
| VN1203 | 2F11 | 629 | C to T | 210 | Pro to Val |
| | | 772 | G to A | 258 | Glu to Lys |
| | 2D9 | 700 | A to G | 234 | Lys to Glu |
| | 4F8 | 613 | A to G | 205 | Lys to GLU |
| VN1203 (K198M) | 9C1 | 614 | T to A | 205 | Met to Lys |

MAbs 6C6, 3D4 and 8H12 Recognize Neuraminidase from H5N1.

1. Recombinant Neuraminidase Expressed in Baculovirus/Sf9 System was Used to Verify Reaction Between mAb 6C6 and Neuraminidase.

Viral RNA was isolated from virus-infected MDCK cells using LS Trizol reagent (Invitrogen) as specified by the manufacturer. Reverse transcription and PCR were performed to amplify the neuraminidase gene H5N1/PR8 using the primers N1 (entry)F (CACCATGAATCCAAATCAGAAGATAA-CAACC; SEQ ID NO:1) and N1(entry)R (CTTGTCAATG-GTGAATGGCAA; SEQ ID NO:2). The PCR product was cloned into pGEM-T Easy cloning vector (Promega, WI, USA) by following the manufacturer's instructions. The recombinant plasmid containing the sequence encoding the neuraminidase was sequenced and confirmed consistent with the reference sequence in the database. The neuraminidase gene was subcloned into the vector of pENTR/TEV/D-TOPO as a transient step, then inserted to baculovirus following Gateway System guide from the supplier (Invitrogen, CA, USA). The recombinant baculovirus with neuraminidase gene was used to transfect Sf9 insect cells and expressed as taught by the supplier (Invitrogen). The Sf9 insect cells with expressed neuraminidase was fixed and IFA was carried out with mAb 6C6, as with the IFA procedure with MDCK cells taught above.

Figures 5A, 5B:
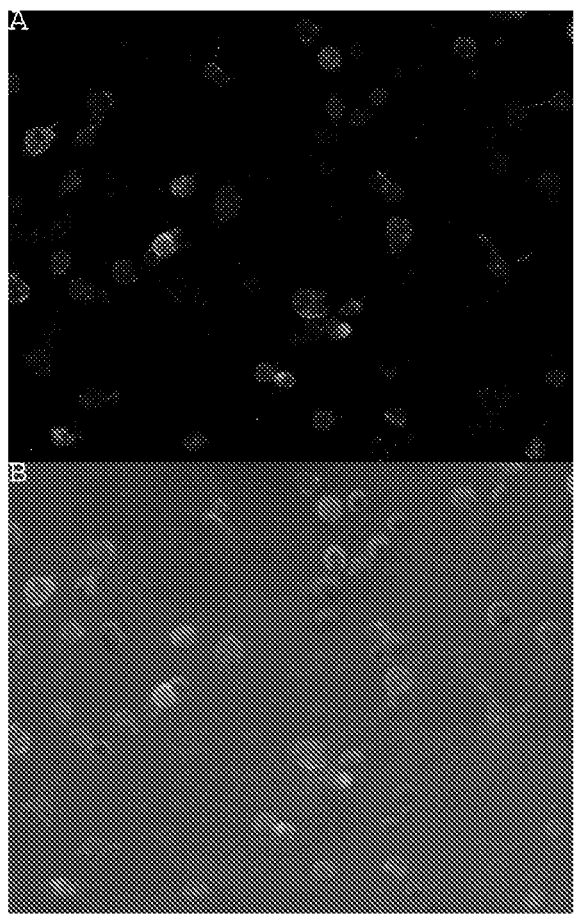
FIGS. 5A and 5B show the typical reaction between mAb 6C6 or 3D4 and expressed recombinant N1.

FIGS. 5A and 5B show the typical reaction between mAb 6C6 and expressed recombinant N1. The reaction of mAb 3D4 and expressed recombinant N1 is similar. FIG. 5A shows the expressed recombinant N1 being detected in Sf9 cells. In FIG. 5B, the merge of ultraviolet light and normal light indicated the individual cells.

2. The Epitopes of mAbs 6C6 and 3D4 are Conformational Rather than Linear.

The Sf9 insect cells were infected by baculovirus with NA insertion and incubated for 96 hours at 28° C. The cells were collected, mixed with sample buffer and loaded to SDS-PAGE gel for staining with Coomassie blue and Western-blotting with (anti-H5N1 mouse serum of) mAb6C6 or mAb 3D4, respectively. The Western-blotting verified the expression of recombinant NA in Sf9 cells. There was no signal band for mAb 6C6 or 3D4 by Western-blotting, which indicated the epitopes of mAbs 6C6 and 3D4 is conformational.

Figure 6A:
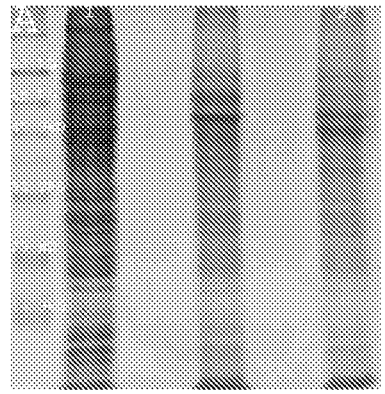
FIGS. 6A and 6B show SDS-PAGE and Western blotting to verify expressed NA.
Figure 6B:
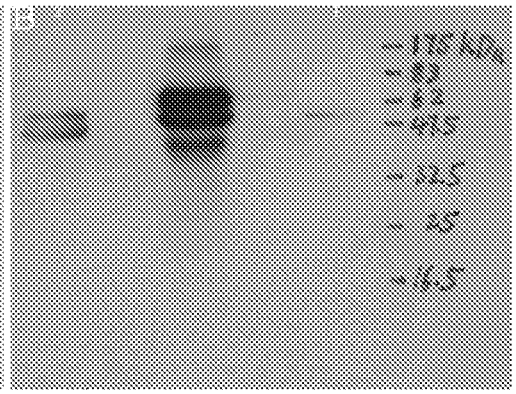

FIGS. 6A and 6B show SDS-PAGE and Western blotting to verify expressed NA.

FIG. 6A shows that the molecular weight of NA is about 49 kDa on the SDS-PAGE gel. In FIG. 6B the Western blotting showed recombinant NA reacting with anti-H5N1 mouse serum as antibody.

Prophylaxis and Therapeutics

Based upon the ability of mAb 5C5 to neutralize H5N1 on both MDCK cells and chicken embryos and its IgG2a isotype, mAb 5C5, and recombinant antibodies comprising the variable region of that antibody, are useful for both prophylaxis and therapeutics. It is commonly accepted, based on studies in mice (19, 20, 21), that neutralizing IgG antibodies have both prophylactic and therapeutic abilities.

Similarly, in view of the ability of mAbs 2D9, 2F11, 3H11, 9C1 and 4F8 to neutralize H5N1 on MDCK cells and their IgG1 or IgM isotype, these mAbs, and recombinant antibodies comprising the variable region of those antibodies, are useful for both prophylaxis and therapeutics.

The following tests illustrate the prophylactic and therapeutic characteristics of mAb 5C5:

Groups of 6 female BALB/c mice (6-8 weeks old) were used as an animal model to study the protection from a lethal challenge of virus by administering mAb 5C5. Inoculation of mice and blood harvests were performed in a biosafety cabinet by personnel wearing powered air purifying respirators. Influenza-infected animals were housed in a biosafety level 3(BSL3) animal facility.

To evaluate the efficacy of the monoclonal antibody as a prophylactic agent (i.e., prior to virus infection) in an animal model, purified mAb 5C5 was administered at a dose of 10 mg/kg intraperitoneally (i.p.) into mice. Twenty-four hours after i.p. administration, the mice were bled for measurement of HI titers with H5N1, then challenged intranasally (i.n.) with 10 $LD_{50}$ of A/Indonesia/CDC669/H5N1 in 20 µl. The control group (total of 6 mice) received mAb 5C4 of IgG1, which was an in-house murine monoclonal antibody made against bacteria C. jejuni. Mice were observed daily for 14 days for survival analysis. In the control group, 6 of 6 mice died within 10 days post-infection. In contrast, mAb 5C5-treated mice were significantly protected—all 6 of the mice in that group were still alive over the 14-day period of observation. The sera from mAb 5C5-administered mice had more than 64 HI titers with A/Indonesia/CDC669/H5N1. These data indicated that administration of mAb 5C5 of IgG2a can penetrate into blood in mice and eventually facilitate viral clearance in the mouse body.

To evaluate the efficacy of mAb 5C5 for therapeutic treatment, the antibody was administered following virus infection. One day (24 hours) after a lethal dose of 10 $LD_{50}$ of A/Indonesia/CDC669/H5N1 in 20 µL given to each of 6 mice, mAb 5C5 was administered at 10 mg/kg by intraperitoneal injection. The control group (6 mice) received mAb 5C4 of IgG1, which was an in-house antibody made against C. jejuni. In the control group, 6 of 6 mice died within 10 days post-infection. In the mAb 5C5 group, 5 of the 6 mice survived the virus challenge at day 14.

These data indicate that mAb 5C5 is effective by administration even after virus infection, indicating that the antibody can be used for both prophylactic and therapeutic purposes.

Example 4

Antigen Capture ELISA (AC-ELISA) for H5N1 Subtype AIV Identification Using Combination mAb6C6 Against N1-Subtype and mAb5C5 Against H5-Subtype As described above, a sample containing H5N1 virus can be identified as H5 subtype using mAb 5C5 or mAb 5A5 and separately as N1 subtype using mAb 6C6. Samples also can be identified as H5N1 through the use of a combination of one of the former antibodies and the latter antibody. An AC-ELISA was designed to detect H5N1 virus. MAb 5C5 was incubated at 0.5 µg/well in 100 µl/well in 100 µl PBS in the 96-well plate (U96 MaxiSorp NUNC-immuno plate) overnight at 4° C. After rinsing the plate with PBS-T, the coated plate was blocked with 1% bovine serum albumin (BSA) for 1 hour at room temperature. The block solution then was discarded, and inactivated H5N1 isolates diluted in PBS at 20 HA units in 100 µl were added to each well and incubated for 2 hours.

The plates were washed four times in wash buffer PBS-T, and 100 µl of horseradish peroxidase-labeled mAb 6C6 diluted 1/500 were added to each well. The plates were further incubated for 1 hour at room temperature and then washed six times with wash buffer. One hundred microliters of freshly prepared substrate (10 mg of o-phenylenediamine dihydrochloride per 20 ml of 0.05 M phosphate citrate buffer, pH 5.0, containing 0.03% sodium perborate) were added to each well and the plates were incubated at room temperature for approximately 5 minutes. The reaction was stopped with 50 µl of 2N sulfuric acid. The absorbance was measured at 490 nm ($A_{490}$) with an automated plate spectrophotometer (Mitenyi Biotec). H5N1 virus gave a significant $A_{490}$ reading, while H7N1 virus gave as low a reading as negative control. The results, set forth in Table 5, indicated that the combination of mAb 5C5 and mAb 6C6 is useful for the identification of H5N1 AIV. A sample containing H5N1 AIV can be identified using mAb 5C5 and mAb 6C6 separately, but using the antibodies in combination provides a means of limiting the amount of sample needed.

Similarly, the combination of mAb 5A5 and mAb 6C6, or other appropriate combinations of mAbs of this invention, also could be used for H5N1 AIV identification.

TABLE 5

Results of AC-ELISA Using Combination of mAb 5C5 and mAb 6C6 to Identify H5N1

|  | #1 | #2 | #3 |
|---|---|---|---|
| A/Indonesia/CDC644/H5N1 | 1.364 | 1.275 | 1.298 |
| A/Indonesia(CDC623/H5N1 | 1.148 | 1.162 | 1.198 |
| A/Indonesia/CDC594/H5N1 | 0.605 | 0.589 | 0.6 |
| A/Indonesia/CDC329/H5N1 | 1.201 | 1.165 | 1.143 |
| A/chicken/Singpaore/94(H7N1) | 0.206 | 0.197 | 0.193 |
| PBS as negative control | 0.188 | 0.171 | 0.177 |
| Blank | 0.053 | 0.06 | 0.058 |

Example 5

Activity of mAbs 2F11, 9C1 and 3H11

The binding activity of each of mAbs 2F11, 9C1 and 3H11 was evaluated in indirect immunofluorescence assay with H5N1-AIV-infected MDCK cells (IFA), Western blot (WB), hemagglutinin inhibition (HI) and virus neutralization (VN) assays.

The results of the assays are set forth in Tables 6 and 7 below:

TABLE 6

Binding Activity with the escape mutant
K205M from H5N1 AIV (A/Vietnam/1203/2004/H5N1)

| MAB | IFA | WB | HI | VN |
|---|---|---|---|---|
| 2F11 | + | -- | + | + |
| 9C1 | + | -- | + | + |
| 3H11 | -- | -- | -- | -- |

TABLE 7

Binding activity with the escape mutant
K205M from H5N1 AIV (A/Indonesia/CDC669/2206/H5N1)

| Mab | IFA | WB | HI | VN |
|---|---|---|---|---|
| 2F11 | + | -- | + | + |
| 9C1 | + | -- | + | + |
| 3H11 | + | -- | + | + |

The escape mutant K205M was produced from H5N1 AIV (A/Vietnam/1203/2004/H5N1) from screening with mAb 6B8, a monoclonal antibody deposited with the American Type Culture Collection on Mar. 20, 2007, as ATCC CRL PTA-8246. The specific interaction of mAb 9C1 and 2F11 with these K205 mutants suggests the potential application of these two mAbs in inhibiting escape mutant generation together with mAb 6B8.

Example 6

Therapeutic Applications of mAbs 2F11 and 9C1

Both 2F11 and 9C1 are produced from the K205M escape mutant of H5 strain A/Vietnam/1203/2004/H5N1 and as such can be combined with another monoclonal antibody which targets the same mutant but fails to bind, or binds at lower activity, to the wildtype strain, such as mAb 6B8 (as produced by hybridoma 6B8 and deposited with the ATCC on Mar. 20, 2007, in accordance with the Budapest Treaty and give accession number CRL PTA-8246), a mAb which targets wildtype 205K strain in the VN1203 strain, as a therapeutic agent. MAb 9C1 recognizes the K205M mutant but fails to bind to wildtype strain VN1203, which indicates that the mAb targets the epitope of 205 methionine in strain VN1203. A monoclonal antibody cocktail comprising mAbs 9C1 and 6B8 can effectively inhibit H5N1 infection and prevent escape mutants generating in vitro and in vivo.

TABLE 8

HI Activity Comparison of mAbs 6B8 and 9C1

| | Vietnam 1203 (clade 1) | |
|---|---|---|
| Mab | WT205K | K205M |
| 8B6 | + | -- |
| 9C1 | -- | + |

To illustrate the activity of the 6B8 and 9C1 mAbs, 16 HA units of AIV were incubated with the mAbs as shown in the table below for at least one half hour at room temperature. The mixture was inoculated into 10 day old chicken embryos.

The HA titer and livability of the embryos were evaluated daily. The results are shown in Table 9 below:

TABLE 9

| mAB | | 1203 (clade 1, 16HA) |
|---|---|---|
| 6B8 (1 ug) | Virus HA | +2 days p.i. |
| | Chicken survivability | --2 days p.i. |
| 6B8 (1 ug) + | Virus HA | --3 days p.i. |
| 9C1 (0.1 ug) | Chicken survivability | + |
| 6B8 (1 ug | Virus HA | --3 days p.i. |
| 9C1 (1 ug) | Chicken survival | + |
| 6B8 (1 ug) + | Virus HA | --3 days p.i. |
| 9C1 (5 ug) | Chicken survivability | + |
| 9C1 (1 ug) | Virus HA | +1 days p.i. |
| | Chicken survivability | --2 days p.i. |

"--" indicated negative in HA test or chicken embryo death
"+" indicated positive in HA test or chicken embryo survival
p.i. indicated post-infection

REFERENCES

1. Jeffery K. Taubenberger, Ann H. Reidl, Raina M. Lourensl, Ruixue Wang, Guozhong Jin and Thomas G. Fanningl. 2006. Molecular virology: Was the 1918 pandemic caused by a bird flu? Was the 1918 flu avian in origin? Nature. 440:E9-E10.
2. Ann H. Reid, Jeffery K. Taubenberger & Thomas G. Fanning 2004. Evidence of an absence: the genetic origins of the 1918 pandemic influenza virus. Nature Reviews Microbiology 2:909-914.
3. Patrick J Gavin, Richard B Thomson, Jr. 2003. Review of Rapid Diagnostic Tests for Influenza. Clinical and Applied Immunology Reviews 4:151-172.
4. Gregory A. Storch, M D. Rapid diagnostic tests for influenza. 2003. Current Opinion in Pediatrics. 15:77-84.
5. Yuen K Y, Chan P K, Peiris M, Tsang D N, Que T L, Shortridge K F, et al. 1998. Clinical features and rapid viral diagnosis of human disease associated with avian influenza A H5N1 virus. Lancet. 351:467-71.
6. Varghese, J. N. et al. 1998. Drug design against a shifting target: a structural basis for resistance to inhibitors in a variant of influenza virus neuraminidase. Structure 6:735-746.
7. Le, Q. M. et al. 2005. Avian flu: isolation of drug-resistant H5N1 virus. Nature 438: 754.
8. Kiso, M. et al. 2004. Resistant influenza A viruses in children treated with oseltamivir: descriptive study. Lancet 364:759-765.
9. de Jong, M. D. et at. 2005. Oseltamivir resistance during treatment of influenza A (H5N1) infection. N. Engl. J. Med. 353:2667-2672.
10. Russell R J, Haire L F, Stevens D J, Collins P J, Lin Y P, Blackburn G M, Hay A J, Gamblin S J, Skehel J J. 2006. The structure of H5N1 avian influenza neuraminidase suggests new opportunities for drug design. Nature 443, 45-49.
11. Cameron P Simmons, Nadia L Bernasconi, Amorsolo L Suguitan, Jr., Kimberly Mills, Jerrold M Ward, Nguyen Van Vinh Chau, Tran Tinh Hien, Federica Sallusto, Do Quang Ha, Jeremy Farrar, Menno D de Jong, Antonio Lanzavecchia, and Kanta Subbarao. 2007. Prophylactic and Therapeutic Efficacy of Human Monoclonal Antibodies against H5N1 Influenza. PLoS Med. 4:e178.
12. Brendon J Hanson, Adrianus C M Boon, Angeline P C Lim, Ashley Webb, Eng Eong Ooi, and Richard J. Webby. 2006. Passive immunoprophylaxis and therapy with humanized monoclonal antibody specific for influenza A H5 hemagglutinin in mice. Respir Res. 7: 126.

13. Jiahai Lu, Zhongmin Guo, Xinghua Pan, Guoling Wang, Dingmei Zhang, Yanbin Li, Bingyan Tan, Liping Ouyang, and Xinbing Yu. 2006. Passive immunotherapy for influenza A H5N1 virus infection with equine hyperimmune globulin F(ab')2 in mice. Respir Res.; 7: 43.
14. Chen H, Smith G J, Li K S, Wang J, Fan X H, Rayner J M, Vijaykrishna D, Zhang J X, Zhang L J, Guo C T, Cheung C L, Xu K M, Duan L, Huang K, Qin K, Leung Y H, Wu W L, Lu H R, Chen Y, Xia N S, Naipospos T S, Yuen K Y, Hassan S S, Bahri S, Nguyen T D, Webster R G, Peiris J S, Guan Y. 2006. Establishment of multiple sublineages of H5N1 influenza virus in Asia: implications for pandemic control. Proc Natl Acad Sci USA. 103:2845-50.
15. Smith G J, Naipospos T S, Nguyen T D, de Jong M D, Vijaykrishna D, Usman T B, Hassan S S, Nguyen T V, Dao T V, Bui N A, Leung Y H, Cheung C L, Rayner J M, Zhang J X, Zhang L J, Poon L L, Li K S, Nguyen V C, Hien T T, Farrar J, Webster R G, Chen H, Peiris J S, Guan Y. 2006. Evolution and adaptation of H5N1 influenza virus in avian and human hosts in Indonesia and Vietnam. Virology. 350: 258-68.
16. De St. Groth, S. F., and D. Scheidigger. 1980. Production of monoclonal antibodies. Strategy and tactics. J. Immunol. Methods. 35:121.
17. Reed, L. J., and H. Muench. 1938. A simple method of estimating fifty percent endpoints, Am. J. Hyg. 27:493-497.
18. Ausubel, F. M., Brent, R., Kingston, R. E., Moore, D. D., Seidman, J. G., Smith, J. A. and K. Struhl. 1999. Current protocols in molecular biology. John Wiley and Sons, Inc., New York, N.Y.
19. Huber, Victor C., McKeon, Raelene M., Brackin, Martha N., Miller, Laura A., Keating, Rachael, Brown, Scott A., Makarovna, Natalia, Perez, Daniel R., MacDonald, Gene H., McCullers, Jonathan A. 2006. Distinct Contributions of Vaccine-Induced Immunoglobulin G1 (IgG1) and IgG2a Antibodies to Protective Immunity against Influenza. Clin. Vaccine Immunol. 13:981-990.
20. Yuichi Harada, Masamichi Muramatsu, Toshikatsu Shibata, Tasuku Honjo, and Kazumichi Kuroda. Unmutated hnmunoglobulin M Can Protect Mice from Death by Influenza Virus Infection. J. Exp. Med. 197: 1779-1785.
21. Palladino, G, Mozdzanowska, K, Washko, G, Gerhard, W. 1995. Virus-neutralizing antibodies of immunoglobulin G (IgG) but not of IgM or IgA isotypes can cure influenza virus pneumonia in SCID mice. J. Virol. 69:2075-2081.
22. Krystyna Mozdzanowska, Jingqi Feng, and Walter Gerhard. J. 2003. Virus-Neutralizing Activity Mediated by the Fab Fragment of a Hemagglutinin-Specific Antibody Is Sufficient for the Resolution of Influenza Virus Infection in SCID Mice. J. Virol. 77:8322-8328.
23. Lu J, Guo Z, Pan X, Wang G, Zhang D, Li Y, Tan B, Ouyang L, Yu X. 2006. Passive immunotherapy for influenza A H5N1 virus infection with equine hyperimmune globulin F(ab')2 in mice. Respiratory Research. 7:43.
24. Horimoto, T. et al. Antigenic differences between H5N1 human influenza viruses isolsted in 1997 and 2003. *J. Vet. Med. Sci.* 66:303-5.
25. Iwasaki, T., et al. *Acta Neuropathol. (Berl).*, 108:485-92.
26. Steven, J, et al. Structure and receptor specificity of the hemagglutinin from an H5N1 influenza virus. *Science* 312: 404-10.
27. Robert G. Webster, A. G. 1994. *Encyclopedia of Virology,* 2:709-724.

---

The invention claimed is:

1. A binding protein that binds specifically to a conformational epitope of the hemagglutinin envelope glycoprotein of an H5 subtype of avian influenza virus and that has the immunological binding characteristics of monoclonal antibody 3H11 as produced by hybridoma 3H11 which is deposited with the American Type Culture Collection with Accession Number PTA-9374, wherein the conformational epitope includes amino acid 155 (Gly).

2. The binding protein of claim 1 which is a monoclonal antibody, a single chain antibody, an antibody fragment, a chimeric antibody or a humanized antibody.

3. The binding protein of claim 1 which is a monoclonal antibody.

4. Monoclonal antibody 3H11 as produced by hybridoma 3H11 which is deposited with the American Type Culture Collection with Accession Number PTA-9374.

5. A method for detecting H5 subtype avian influenza virus in a biological specimen which comprises contacting the specimen with a binding protein that binds specifically to a conformational epitope of the hemagglutinin envelope glycoprotein of an H5 subtype of avian influenza virus, said binding protein having the immunological binding characteristics of monoclonal antibody 3H11 as produced by hybridoma 3H11 which is deposited with the American Type Culture Collection with Accession Number PTA-9374, wherein the conformational epitope includes amino acid 155 (Gly).

6. The method of claim 5 wherein the binding protein is a monoclonal antibody, a single chain antibody, an antibody fragment, a chimeric antibody or a humanized antibody.

7. The method of claim 5 wherein the binding protein is a monoclonal antibody.

8. The method of claim 7 wherein the monoclonal antibody is antibody 3H11 as produced by hybridoma 3H11 which is deposited with the American Type Culture Collection with Accession Number PTA-9374.

9. The method of claim 5 which comprises contacting the specimen with a second binding protein that specifically binds to the envelope glycoprotein of an H5 subtype of avian influenza virus, wherein the first binding protein is a capture binding protein and the second binding protein is a detector binding protein that contains or is conjugated to a detectable element.

10. The method of claim 9 wherein at least one of the first and second binding proteins is a monoclonal antibody.

11. The method of claim 9 wherein the first and second binding proteins are monoclonal antibodies.

12. The method of claim 9 wherein the first binding protein is immobilized onto a solid surface.

13. The method of claim 9 wherein the second binding protein contains a radioactive atom, is conjugated to a fluorescent molecule, or is conjugated to an enzyme.

14. A kit for detecting H5 subtype avian influenza virus in a biological specimen which comprises a binding protein that binds specifically to a conformational epitope of the hemagglutinin envelope glycoprotein of an H5 subtype of avian influenza virus, said binding protein having the immunological binding characteristics of monoclonal antibody 3H11 as produced by hybridoma 3H11 which is deposited with the American Type Culture Collection with Accession Number PTA-9374 wherein the conformational epitope includes amino acid 155 (Gly), together with at least one reagent for the detection of binding of said binding protein to said envelope glycoprotein.

15. The kit of claim 14 which comprises a second binding protein that specifically binds to the envelope glycoprotein of an H5 subtype of avian influenza virus, wherein the first binding protein is a capture binding protein and the second binding protein is a detector binding protein that contains or is conjugated to a detectable element.

16. The kit of claim 15 wherein at least one of the first and second binding proteins is a monoclonal antibody.

17. The kit of claim 15 wherein the first and second binding proteins are monoclonal antibodies.

18. The kit of claim 15 wherein the first binding protein is immobilized onto a solid surface.

19. The kit of claim 15 wherein the second binding protein contains a radioactive atom, is conjugated to a fluorescent molecule, or is conjugated to an enzyme.

20. A method of treating a subject infected with H5 subtype avian influenza virus which comprises administering to said subject an effective amount of a binding protein that binds specifically to a conformational epitope of the hemagglutinin envelope glycoprotein of an H5 subtype of avian influenza virus and that has the immunological binding characteristics of monoclonal antibody 3H11 as produced by hybridoma 3H11 which is deposited with the American Type Culture Collection with Accession Number PTA-9374, wherein the conformational epitope includes amino acid 155 (Gly).

21. The method of claim 20, wherein the binding protein is a monoclonal antibody, single chain antibody, antibody fragment, chimeric antibody or humanized antibody.

22. The method of claim 20, wherein the binding protein is a monoclonal antibody.

23. The kit of claim 14, wherein the binding protein is monoclonal antibody 3H11 as produced by hybridoma 3H11 which is deposited with the American Type Culture Collection with Accession Number PTA-9374.

24. The method of claim 20, wherein the binding protein is monoclonal antibody 3H11 as produced by hybridoma 3H11 which is deposited with the American Type Culture Collection with Accession Number PTA-9374.

* * * * *